(12) United States Patent
Deutsch et al.

(10) Patent No.: US 12,016,798 B2
(45) Date of Patent: Jun. 25, 2024

(54) METHODS FOR CHARACTERIZING A LASER BEAM OF A LASER PROCESSING SYSTEM, DIAPHRAGM ASSEMBLY AND LASER PROCESSING SYSTEM

(71) Applicant: Carl Zeiss Meditec AG, Jena (DE)

(72) Inventors: Christian Deutsch, Weimar (DE); Gerard Antkowiak, Jena (DE); Martin Hacker, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 211 days.

(21) Appl. No.: 17/641,575

(22) PCT Filed: Sep. 7, 2020

(86) PCT No.: PCT/EP2020/074984
§ 371 (c)(1),
(2) Date: Mar. 9, 2022

(87) PCT Pub. No.: WO2021/048071
PCT Pub. Date: Mar. 18, 2021

(65) Prior Publication Data
US 2022/0296418 A1 Sep. 22, 2022

(30) Foreign Application Priority Data

Sep. 10, 2019 (DE) ...................... 10 2019 124 164.2
Sep. 10, 2019 (DE) ...................... 10 2019 124 166.9
Sep. 10, 2019 (DE) ...................... 10 2019 124 258.4

(51) Int. Cl.
*A61F 9/008* (2006.01)

(52) U.S. Cl.
CPC .............................. *A61F 9/00814* (2013.01); *A61F 2009/00855* (2013.01); *A61F 2009/00872* (2013.01)

(58) Field of Classification Search
CPC ........ A61F 9/00814; A61F 2009/00855; A61F 2009/00872
See application file for complete search history.

(56) References Cited

U.S. PATENT DOCUMENTS 5,376,086 A * 12/1994 Khoobehi ........... A61F 9/00804
606/4
5,391,886 A * 2/1995 Yamada .............. H01J 37/3174
250/398

(Continued)

FOREIGN PATENT DOCUMENTS

EP   1 211 996 A1   6/2002
WO   01/87199 A2    11/2001

OTHER PUBLICATIONS

International Search Report of PCT/EP2020/074984 with English translation.

*Primary Examiner* — Eric D. Bertram
(74) *Attorney, Agent, or Firm* — Tautz & Schuhmacher LLC; Georg Hasselmann

(57) ABSTRACT

The claimed embodiments relate to methods for characterizing a laser beam (24) of a laser processing system (30). The method includes a) providing an aperture arrangement (10) with a plurality of apertures (14) in a work plane (300) of the laser processing system (30) such that the apertures (14) extend within the work plane (300). The method also includes b) scanning the laser beam (24) along a scanning direction (200) parallel to the work plane (300) across the aperture arrangement (10) in such a way that the laser beam (24) at least partially sweeps over the apertures (14). The method also includes c) determining a respective energy of the laser beam (24) transmitted through the apertures (14) during the scanning process, and d) determining an extent of the laser beam (24) along the scanning direction (200) using the determined energy of the laser beam (24) transmitted through a first aperture (14a) of the plurality of apertures (14) and determining an energy parameter of the laser beam (24) on the basis of the determined energy of the laser beam (24) transmitted through a second aperture (14b) of the plurality of apertures (14). In this case, the first aperture (14a) has a predetermined extent along the scanning direction (200), which is smaller than the mean diameter of the laser beam (24) in the work plane (300). In addition, a second aperture (14b) has an extent that is larger than the laser beam (24) in the work plane (300) and is designed to transmit the laser beam (24) essentially completely.

9 Claims, 13 Drawing Sheets

(56) References Cited

U.S. PATENT DOCUMENTS

| | | | | |
|---|---|---|---|---|
| 6,313,910 B1* | 11/2001 | Garvey | ............. | G01J 1/4257 |
| | | | | 356/121 |
| 6,559,934 B1* | 5/2003 | Yee | ............. | B23K 26/705 |
| | | | | 606/4 |
| 7,022,117 B1* | 4/2006 | Hohla | ............. | A61F 9/008 |
| | | | | 606/5 |
| 8,758,331 B2* | 6/2014 | Lubatschowski | ....... | A61F 9/008 |
| | | | | 606/4 |
| 10,085,886 B2* | 10/2018 | Schuele | ............. | A61F 9/00827 |
| 2002/0198515 A1* | 12/2002 | Somani | ............. | B23K 26/705 |
| | | | | 606/4 |
| 2013/0237972 A1* | 9/2013 | Raksi | ............. | A61F 9/0084 |
| | | | | 606/6 |
| 2014/0316389 A1* | 10/2014 | Schuele | ............. | A61F 9/00836 |
| | | | | 606/5 |
| 2022/0209410 A1* | 6/2022 | Lilja | ............. | C03C 17/06 |
| 2023/0134190 A1* | 5/2023 | Romano | ............. | A61F 9/00827 |
| | | | | 606/5 |

* cited by examiner

METHODS FOR CHARACTERIZING A LASER BEAM OF A LASER PROCESSING SYSTEM, DIAPHRAGM ASSEMBLY AND LASER PROCESSING SYSTEM

The claimed embodiments relate to methods for characterizing a laser beam of a laser processing system, an aperture arrangement and a laser processing system, in particular for ophthalmic surgery on an eye. The embodiments consequently lie in the field of laser processing systems for ophthalmic surgery.

Visual defects of the human eye can frequently be traced back to an inadequate refractive effect of the eye. By way of example, these may be caused by corneal distortions. In many cases, the causes of the visual defects can be removed or reduced by means of ophthalmic or refractive surgery. To carry out such a refractive surgical treatment, for example refractive corneal surgery, use is usually made of excimer lasers, by means of which material is ablated from the cornea to be corrected in order to provide the cornea with the desired refractive effect. It is understood that the refractive effect must be corrected very precisely in order to obtain a satisfactory treatment result, within the scope of which the correction attains the desired refractive effect.

For the purposes of obtaining the required precision during material ablation from the cornea by means of a laser beam from an excimer laser, and for regulatory reasons, there is the need to regularly characterize or verify the actual material ablation brought about by the laser beam. The laser beam is usually present in pulsed form such that the material ablation by the laser beam is typically determined as material ablation per laser pulse or "shot", or for a predetermined pulse sequence or shot sequence (laser pulse number). In the case of continuously operating lasers, the material ablation is determined per unit of irradiation time.

Such a characterization of the material ablation is frequently also referred to as "fluence test" since the fluence, as ratio of laser pulse energy to effective laser spot diameter, is usually the most important characteristic for material ablation if the material strongly absorbs the laser light, as is the case, for example, for UV light of the excimer lasers in plastics or biological tissues.

Various excimer laser systems for refractive correction of the cornea are known in the prior art, for example the systems by the applicant designated MEL 80 and MEL 90. In these and other systems, the material ablation can be regularly verified by means of so-called fluence papers, which typically consist of colored cardboard on which a metal-coated plastic film with a known thickness has been adhesively bonded. In this context, a predetermined shot pattern impinges on the fluence paper for the purposes of verifying the material ablation, with a certain number of pulses or shots, that is to say certain shot number ratios, respectively impinging on different test sites on the fluence paper. Thereupon, the material ablation on the respective test sites of the fluence paper caused thereby is verified with the naked eye, with the metal-coated plastic film still being maintained in or at the test sites for some predetermined shot sequences while being partly ablated at test sites by other shot sequences, for example with a higher shot number, which correspond to a flux of +4%. At the test sites where the metal-coated plastic film was at least partly ablated, the colored cardboard arranged under the originally applied metallic plastic film is visible, at least in portions. The verification is then implemented by the user using their naked eye.

An alternative method for characterizing the laser beam consists of working a lens profile into a substrate made of PMMA by means of the excimer laser by virtue of material being ablated appropriately from the PMMA substrate by means of the excimer laser. Subsequently, there is a complicated measurement of the processed PMMA substrate, within the scope of which the actual refractive power of the processed PMMA substrate or its lens shape is measured and compared to the corresponding, predetermined target value. Thereupon, the effect of the processing can be deduced on the basis of possible deviations and the laser beam can be characterized. However, this method requires specific measuring devices and a great amount of effort, and so regular verification of the laser beam on a daily basis by way of such a method is not sensible or possible from an economical point of view. Moreover, carrying out such a method requires a great amount of technical expertise and is often left to specially trained staff, for instance a service technician, for this reason, and it cannot simply be carried out by a regular operator. Therefore, such a method is typically only carried out within the scope of a first time calibration, for example during the production or initial commissioning of the system.

The prior art has also disclosed a method for determining the dimensions of a laser beam, in which the laser beam is scanned along a path over a reference edge, for example as described in U.S. Pat. No. 6,559,934 B1. Further, US 2002/0198515A1 describes a method in which a structure in a treatment plane is used for the adjustment of a laser system, said structure having a slot or a reference edge for the purposes of adjustment or calibration. Moreover, WO 01/87199 A2 describes an apparatus and a method for measuring the energy and/or position of a pulsed laser beam, in which the laser beam is intermittently steered toward a sensor.

An additional target laser must frequently be used in the case of invisible processing lasers, which emit in the ultraviolet or infrared spectral range, for example. This target laser must emit in the visible spectral range and, for reasons of laser safety, usually have a much lower intensity in the work plane than the processing laser. This target laser and the processing laser are typically spatially superimposed sufficiently well in the work plane, wherein this spatial superposition should be verified regularly for reasons of safety. Conventionally, this superposition is frequently verified visually by the physician by virtue of the overlap of structures marked by means of processing lasers and the target laser being examined, for example on fluence papers.

It is therefore the object to provide a method and an apparatus which facilitate a reliable characterization or verification of a processing laser in the work plane and offer the option of automation. In this context, the characterization should especially comprise the fluence and/or spatial calibration of the laser parameters in the work plane.

It is further an object to provide a method and an apparatus which facilitate the verification of the superposition of processing laser and target laser and which offer the option of automation.

This object is achieved by the described embodiments. The embodiments relate to a method for characterizing a laser beam of a laser processing system, an aperture arrangement, a laser processing system having the features of the respective independent claims, an apparatus for refractive correction of the cornea, an excimer laser and an apparatus for refractively correcting a cornea. Optional embodiments are specified in the dependent claims and in the description.

A first embodiment relates to a method for characterizing a laser beam of a laser processing system. The method comprises a) providing an aperture arrangement with a plurality of apertures, that is to say with two or more apertures, in a work plane of the laser processing system, in such a way that the apertures extend within the work plane. Further, the method comprises b) scanning the laser beam over the aperture arrangement along a scanning direction parallel to the work plane, in such a way that the laser beam at least sweeps partly over at least two of the apertures successively. Moreover, the method comprises c) determining a respective energy of the laser beam transmitted through the apertures during the scanning procedure and d) determining an extent of the laser beam along the scanning direction on the basis of the determined energy of the laser beam transmitted through a first aperture of the plurality of apertures and determining an energy parameter of the laser beam on the basis of the determined energy of the laser beam transmitted through a second aperture of the plurality of apertures. In this case, the first aperture has a predetermined extent along the scanning direction which is smaller than the mean diameter of the laser beam in the work plane. Moreover, the second aperture has an extent in the work plane that is greater than the laser beam in the work plane and that is designed to substantially fully transmit the laser beam. Optionally, the laser beam sweeps over the apertures in such a way that, at any one time, no more than one of the apertures is swept over by the laser beam, and not a plurality of apertures being simultaneously swept over by the laser beam.

A further embodiment relates to an aperture arrangement for characterizing a laser beam of a laser processing system, the aperture arrangement being arrangeable in a work plane of the laser processing system and comprising a stop having a plurality of apertures. In this case, the aperture arrangement comprises a first aperture of the plurality of apertures which has a predetermined extent along a scanning direction of the laser beam which is smaller than the mean diameter of the laser beam to be tested in the work plane, and a second aperture of the plurality of apertures which has an extent which is greater than the laser beam to be tested and which is designed to substantially fully transmit the laser beam. Moreover, the aperture arrangement comprises at least one photodetector which is arranged such that at least a part of the laser beam which has been transmitted through the apertures in the work plane is detectable by means of the photodetector.

A further embodiment relates to a laser processing system for processing an object in a work plane by means of a laser beam. The laser processing system comprises a laser source for providing the laser beam, a deflection device, by means of which the laser beam is movable within the work plane perpendicular to the propagation direction of the laser beam, and an aperture arrangement according to an optional embodiment. For the purposes of characterizing the laser beam, the aperture arrangement is arrangeable in the laser processing system in such a way in this case that the apertures are arranged in the work plane.

A further embodiment relates to a method for characterizing a laser beam of a laser processing system. The method comprises (a) providing an aperture arrangement with an aperture in a work plane of the laser processing system, in such a way that the aperture extends within the work plane, the aperture arrangement having at least two aperture edges which lie opposite one another at a predetermined distance and which extend parallel to one another, said aperture edges delimiting the aperture, and the aperture being larger than the laser beam in the work plane and being designed to substantially fully transmit the laser beam. Further, the method comprises (b) scanning the laser beam over the aperture arrangement along a scanning direction parallel to the work plane, in such a way that the laser beam in each case at least sweeps partly over a first aperture edge of the two aperture edges, the aperture and a second aperture edge of the two aperture edges successively in time, and (c) determining an energy of the laser beam transmitted through the aperture during the scanning procedure. Moreover, the method comprises (d) determining an extent of the laser beam along the scanning direction on the basis of a transmitted energy curve when sweeping over the first and/or the second aperture edge by means of the laser beam and determining an energy parameter of the laser beam that has been substantially fully transmitted through the aperture, and (e) determining an alignment parameter of the laser processing system on the basis of the laser beam sweeping over the aperture edges arranged at the predetermined distance.

A further embodiment relates to a method for characterizing a laser beam of a laser processing system. This further embodiment may optionally comprise the first embodiment. The method comprises determining an energy parameter of the laser beam. Moreover, the method comprises providing a calibration device in a work plane of the laser processing system and having the laser beam impinge on the calibration device under the same conditions as are provided for the use of the laser beam for processing a processing object, and determining a calibration parameter by means of the calibration device in the work plane. Further, the method comprises providing the calibration device in a verification plane outside of the work plane and deflecting the laser beam in such a way that the laser beam impinges on the calibration device in the verification plane, and determining a verification parameter by means of the calibration device in the verification plane. Moreover, the method comprises determining a deviation factor which characterizes a deviation between the calibration parameter and the verification parameter, and characterizing the laser beam by means of the calibration device in the verification plane using the deviation factor.

A further embodiment relates to a laser processing system for processing a processing object by means of a laser beam. The laser processing system comprises an energy sensor which is designed to determine an energy parameter of the laser beam. Further, the laser processing system comprises a calibration device which has a choice of being arrangeable in a work plane of the laser processing system and being able to be impinged by the laser beam and of being arrangeable in a verification plane outside of the work plane and being able to be impinged by the laser beam, and a deflection element which is arrangeable in the beam path of the laser beam, in such a way that the deflection element deflects the laser beam, which is directed at the work plane, into the verification plane. In this case, the laser processing system is configured to arrange the calibration device in the work plane and determine a calibration parameter, to arrange the calibration device in the verification plane and determine a verification parameter, to determine a deviation factor which characterizes a deviation between the calibration parameter and the verification parameter, and to characterize the laser beam by means of the calibration device in the verification plane using the energy parameter and the deviation factor.

A further embodiment relates to a method for characterizing a laser beam, which can be used as an alternative to or in combination with the above-described first embodiment, and which may likewise be part of the further embodiment of the method for characterizing a laser beam. The method comprises having the laser beam impinge on a test object, in such a way that the laser beam ablates some of the material of the test object at a test site of the test object. Further, the method comprises determining a change in the thickness of the test object at the test site on account of the laser beam impinging thereon.

A further embodiment relates to an apparatus for characterizing a laser beam. In this case, the apparatus comprises a test object holder which is designed to provide a test object for the laser beam to impinge on the test object so that some of the material of the test object is ablatable from a test site of the test object by means of the laser beam. Moreover, the apparatus comprises a measuring device which is configured to determine a change in the thickness of the test object at the test site on account of the laser beam impinging thereon.

A further embodiment relates to an excimer laser comprising an apparatus for characterizing the laser beam according to an optional embodiment.

A further embodiment relates to an apparatus for refractive correction of the cornea, comprising an excimer laser according to a preferred embodiment and/or an apparatus for characterizing a laser beam according to a preferred embodiment.

In this case, a laser beam is the radiation emitted by a laser, optionally an excimer laser. The laser beam need not necessarily have continuous wave radiation but may also be present in pulsed form. Further, the laser beam may be present in collimated and/or convergent and/or divergent form for the characterization. The laser beam optionally has electromagnetic radiation in the ultraviolet spectral range. Further optionally, the laser beam has a central wavelength at approximately 193 nm. Optionally, the laser beam is in the form of a laser beam for a refractive correction of the cornea and is optionally provided by an excimer laser. The laser beam is particularly optionally provided by an ArF excimer laser. Here, a work laser beam of the laser processing system is referred to as laser beam. In addition to the laser beam, that is to say in addition to the work laser beam, the laser processing system according to optional embodiments may also provide a target laser beam, which for instance is of lower energy and whose optical spectrum is optionally located at least partly within the visible spectral range. However, the latter is always referred to as target laser beam, to distinguish it from the laser beam.

The characterization of the laser beam optionally comprises the characterization of the beam profile of the laser and/or the characterization of a beam size. Optionally, the characterization may further comprise a characterization of an energy, for instance a pulse energy, and/or a peak power and/or an average power and/or the energy of a predetermined sequence or number of pulses and/or an intensity and/or a fluence (in particular in the work plane) and/or material ablation obtainable therewith. The characterization may further optionally comprise a characterization of a focus of the laser beam, for instance a shape and/or a profile and/or an intensity of the focused laser beam.

In this case, an aperture arrangement is an arrangement or apparatus which comprises a stop with a plurality of apertures. For example, the stop can have a planar embodiment and the apertures can be formed as cutouts in the stop. Apart from the apertures, the stop is opaque to the laser radiation and optionally formed in such a way that having the laser beam impinge on the stop does not damage the latter in a way that would impair the opaqueness to the laser radiation. The apertures optionally have a fully transparent form for the laser radiation and particularly optionally are in the form of cutouts or holes in the stop. The stop may have an integral or multi-part embodiment. Apart from the stop, the aperture arrangement may have even further elements. By way of example, the aperture arrangement may have a photodetector and/or other elements, which for example may form a fixed constituent part of the aperture arrangement.

In this case, the work plane is the plane in which the laser processing system has the laser beam impinge on a processing object, for example of an eye, in order to process the processing object. Expressed differently, the laser processing system may be designed to process a processing object in the work plane using the laser beam and/or to mark the point of incidence on the processing object using the target laser beam. By way of example, the laser beam and/or the target laser beam may be focused into the work plane by the laser processing system. However, the work plane need not necessarily be a plane in the mathematical sense in this case, although this may be the case according to some optional embodiments. According to other optional embodiments, the work plane may also be formed as a curved surface and therefore represent a surface extending in three-dimensional space.

In this case, scanning the laser beam along the scanning direction optionally is a deflection of the laser beam such that the point of intersection of the laser beam with the work plane displaces or moves along the scanning direction within the work plane. By way of example, scanning may be brought about by means of a deflection device which can move the laser beam in a predetermined region within the work plane. In this case, the scanning direction need not necessarily run along a straight line, but may also follow a curved path or even a free-form curve. The scanning direction may also extend in a plurality of dimensions. Optionally, the scanning direction respectively runs in a straight line in a plurality of scan portions, with the scanning directions of the individual scan portions possibly being different from one another and possibly even being perpendicular to one another. Particularly optionally, the scan direction runs in discontinuous fashion and with jumps between the individual processing points in order to position the processing points for successive instances of processing as far apart from one another as possible, for the purposes of reducing the thermal load on the processing object. However, the scanning direction optionally runs completely within the work plane.

According to another optional embodiment, scanning the laser beam over the aperture arrangement can be implemented alternatively or in addition by virtue of the aperture arrangement being moved relative to, optionally moved perpendicular to, the laser beam. This may offer the advantage that the laser beam need not necessarily be deflected for the characterization. Scanning the laser beam over the aperture arrangement along a scanning direction parallel to the work plane in this case means that the laser beam is deflected in one or more directions perpendicular to the optical axis of the laser beam. In this case, the distance between the work plane and the optical element causing the deflection, for instance a scanner mirror, is optionally so large that the possible projection effects during the deflection of the laser beam, that is to say during scanning, are negligible, especially for a determination of the fluence.

The laser beam at least sweeping partly over the apertures in this case means that the laser beam does not necessarily sweep over all apertures. This also means that, optionally, the laser beam does not necessarily sweep over the entire respective aperture but that the aperture may also have regions over which the laser beam does not sweep. By way of example, a first aperture according to an optional embodiment may be in the form of a slot, the width of the slot being smaller than the laser beam in the work plane and the length of the slot being greater than the extent of the laser beam in the work plane. By way of example, the laser beam may sweep over such a slot-shaped aperture in such a way that although the laser beam sweeps over the entire width of the aperture, it does not sweep over the full length.

In this case, the mean diameter optionally is the full width at half maximum (FWHM). In this case, the extent of the laser beam is optionally the beam area which contains 99.5% of the power or energy of the laser beam under the assumption of a Gaussian beam profile. The second aperture substantially fully transmitting the laser beam in this case means that the power or energy not transmitted or blocked by the second aperture makes up no more than 0.5% of the overall power or overall energy. As a result, the attenuation of the laser beam by the second aperture is vanishingly small and optionally below a typical sensor signal-to-noise ratio.

An energy parameter determined within the scope of the method in this case optionally is such a parameter which characterizes the energy and/or power of the laser beam. Optionally, the intensity and/or fluence of the laser beam in the work plane is determinable together with the determined extent of the laser beam.

Optionally, the energy parameter characterizes an energy of the laser beam and/or a power of the laser beam and/or an energy of a laser pulse and/or an energy of a series of laser pulses.

In this case, a calibration parameter determined within the scope of the method is a parameter, on the basis of which it is possible to determine and/or anticipate material ablation by the laser beam, in particular ablation of the cornea during the application of said laser beam on an eye to be treated. In particular, the calibration parameter may comprise the fluence and/or intensity of the laser beam in the work plane, or facilitate the determination of the fluence and/or intensity of the laser beam in the work plane. Optionally, the verification parameter corresponds to the calibration parameter, with the stipulation that the verification parameter characterizes the laser beam in the verification plane. Particularly optionally, the calibration parameter and the verification parameter are directly comparable with one another such that the deviation factor optionally represents a dimensionless quantity which quantifies a difference in the values or absolute values or amplitudes of the calibration parameter on the one hand and of the verification parameter on the other hand. Optionally, the determination of a calibration parameter comprises a determination of a fluence and/or an intensity of the laser beam in the work plane, wherein the determination of a verification parameter comprises a determination of a fluence and/or an intensity of the laser beam in the verification plane.

In this case, the verification plane is a plane in which the verification parameter is provided by means of the calibration device. Optionally, the verification parameter in the verification plane is determined in the same way as the calibration parameter is determined in the work plane. In this case, the verification plane is arranged such that the calibration device can be arranged in the verification plane even if a patient has adopted the treatment position and a patient's eye is arranged in the work plane. Optionally, the verification plane is accordingly arranged in such a way and/or the calibration device is provided in the verification plane in such a way that there is no spatial overlap between the calibration device provided in the verification plane and a processing object arranged in the work plane. Particularly optionally, the verification plane is at least partly arranged within the laser processing system and/or the calibration device, when provided in the verification plane, is arranged within the laser processing system. This offers the advantage that the laser processing system may have a particularly compact form.

The test object optionally is a solid-state element, from which material can be ablated by way of laser ablation by the laser beam. Further optionally, the test object is designed to at least partly absorb the radiation of the laser beam in order to reach material ablation by way of the absorbed energy, which was radiated in in the form of the laser beam. Expressed differently, the test object optionally consists of a UV-ablatable medium. Further optionally, the test object is made of a material which is at least partly transparent and optionally virtually completely transparent to electromagnetic radiation in the visible and/or infrared spectral range. This facilitates the use of optical measuring methods on the basis of visible and/or infrared wavelengths for the purposes of determining the change in the thickness of the test object. Further optionally, the test object is designed in such a way that the latter has a surface which can be registered by means of a confocal-chromatic sensor, in particular after the surface was processed by a UV laser.

Particularly optionally, the test object consists at least in part of PMMA (polymethylmethacrylate), which has a very high optical density in the ultraviolet spectral range, in particular at 193 nm, and which has great transparency especially in the visible spectral range. As an alternative or in addition to solid test objects it is also possible to use test objects that have or consist of a biological tissue, for instance donor corneal parts, or else gel-like substances, for instance agar-agar. In this case, it is particularly advantageous if the test object need not be moved or need only be moved very little between laser processing and measurement and if the measurement can be implemented in a very timely fashion after the laser beam has impinged thereon so that the risk of a change in shape of the test object between processing and measurement can be largely reduced or eliminated.

Optionally, the determination of the change in the thickness of the test object is implemented with a position and/or orientation of the test object that has not been changed from when the laser beam impinged on the test object. Expressed differently, the test object optionally is substantially not moved from when the laser beam impinges thereon until the change in the thickness is determined. In this context, "substantially not moved" means that there is no movement of the test object relative to the laser beam and/or relative to the measuring device, or that any possible movement is so small that this does not impair the determination of the change in the thickness at the test site. This further offers the advantage that the change in the thickness can reliably be determined at the test site on which the laser beam impinged. Further, this offers the advantage that it is also possible to reliably use such test objects whose form is not stable and/or whose positionability is not reliably reproducible.

Impinging the laser beam on the test object optionally comprises the test object being exposed to the laser beam such that the laser beam is incident on the test object. The laser beam impinging on the test object is optionally implemented with a certain irradiation duration, in particular when continuous wave lasers are used, or else with a certain number of laser pulses when a pulsed laser is used. It is understood that a relationship and/or a correlation between the material ablation and the irradiation duration or the number of laser pulses exist when the laser beam impinges on the test object. Optionally, the impingement is the same as when the laser beam impinges on the cornea during the refractive correction of the cornea, in particular the same in respect of ambient parameters such as for instance UV-absorbing substances in the ambient air, for instance humidity, and/or in respect of the beam diameter and/or the beam power or pulse energy.

Alternatively or in addition, the test object may also be impinged with different beam diameters and/or powers and/or pulse energies.

In this case, the test site is, in particular, a site in and/or on the test object, which may be located on a surface of the test object or within the test object, that is to say in the volume region of the test object. In this case, the test site is the site on which the laser beam impinges and where material ablation occurs accordingly. Before the laser beam impinges on the test site, the test site may optionally correspond to the unmodified test object and might not differ from other sites on the test object.

The embodiments offer the advantage that both the extent of the laser beam and also the power or energy of the laser beam can be measured directly in the work plane. This is advantageous in that the fluence of the laser beam can be determined directly in the work plane, that is to say at the site where the laser beam is applied to the processing object, without error-prone assumptions or influences, and this allows implementation of a particularly reliable characterization and optional adjustment of the laser beam. Consequently, this offers the advantageous option of directly determining, e.g., the fluence without for example having to carry out energy or power measurements at a different site in the laser processing system and without having to determine the extent of the laser beam outside of the work plane so as to have to deduce the fluence indirectly, possibly using inapplicable assumptions. This also offers the option of optionally being able to verify the exact position of the laser beam and also the exact position of a target laser beam and optionally the overlap thereof in the work plane. Therefore, the reliability of the characterization can be increased by the embodiments.

Moreover, the embodiments offer the advantage that an aperture arrangement can be used both for a characterization of the laser beam and especially a determination of the fluence of the laser beam, and for a calibration of a deflection device, for instance a scanner. Expressed differently, the embodiments offer the advantage that it is possible to carry out a plurality of characterizations or verifications or characterizations by means of an aperture arrangement in the work plane, for which different apparatuses are conventionally required. In this way, the characterization or verification or calibration of the laser processing system can be simplified in terms of hardware requirements and/or accelerated in terms of time outlay, and so the acquisition and/or operational costs can be reduced and the servicing times can be shortened. This also offers the advantage that optionally the exact position of the laser beam and optionally the exact position of the target laser beam and hence the overlap thereof in the work plane can be verified, as a result of which the safety of the laser processing system can be increased.

Moreover, this offers the advantage that only one photodetector or energy sensor is required for the characterization. This is particularly advantageous in view of the fact that the technical requirements for the characterization can be chosen to be less than in the prior art and that possible deviations between the measurements of a plurality of energy sensors, as used conventionally, can be avoided, and hence the risk of falsification of the characterization can be reduced.

Moreover, the embodiments offer the advantage that the fluence or target fluence, to which the laser system is calibrated, can be stored as a quantity that is dependent on the beam diameter so that hence the calibration is not directed at the individual parameters of extent of the laser beam and energy separately—that is to say, a separate calibration of energy and spot size is verified on an individual basis in each case—but that both values are calibrated or characterized in combination and the dependencies thereof can be taken into account in the process. By way of example, such a dependence may consist in the fact that the fluence required for a certain ablation volume may be determined in accordance with a nonlinear function of the spot size of the laser beam in the work plane.

Additionally, the embodiments offer the advantage that the fluence of the laser beam can be determined directly in the work plane and, accordingly, the scope of the characterization may also comprise monitoring of the fluence in respect of predetermined tolerance limits. In conventional methods known from the prior art, a plurality of power or energy parameters and a size of the laser beam are frequently determined independently of one another and are verified in respect of their respective tolerance limits without however being able to determine the fluence in the work plane. This leads to the respective tolerance limits for the individual parameters having to be chosen very narrow in the prior art. According to some embodiments, it is possible to determine the fluence and check it against possible predetermined tolerance limits such that a combination of individual deviations of energy and beam diameter, which nevertheless keep the fluence in the tolerance range, need not incorrectly be assessed as a defect.

Some embodiments offer the advantage that the characterization of the laser beam may optionally be automated. To this end, it may be particularly advantageous if the laser processing system is designed to independently or automatically arrange the aperture arrangement in the work plane and, following the characterization of the laser beam, to independently or automatically remove said stop arrangement from the work plane again.

The embodiments offer the advantage that the characterization of the laser beam can be implemented using only one calibration device, even though a plurality of calibration devices may also be used according to some embodiments. As a result of one calibration device being sufficient, it is possible to avoid deviations and falsifications of the characterization of the laser beam on account of differences between separate calibration devices.

Further, some embodiments offer the advantage that there can initially be a proper calibration in the work plane and the laser beam can subsequently be briefly characterized or monitored on the basis of the verification parameter and the energy parameter by virtue of the laser beam being deflected into the verification plane, especially during processing or treatment when a calibration plane cannot be arranged in the work plane. Although the characterization in the verification plane may not allow a calibration in the true sense of the word, for example because a calibration in the work plane is necessarily prescribed, the characterization in the verification plane may nevertheless offer valuable additional information in respect of whether one or more parameters of the laser beam have changed since the last calibration or characterization and/or whether a renewed calibration appears advantageous or necessary. In this way, the interval between calibrations and/or characterizations in the work plane may optionally be lengthened and/or a more regular characterization of the laser beam may be facilitated, in particular within time portions where the patient is already in or still in the work plane.

Moreover, some embodiments offer the advantage that the characterization can be implemented particularly reliably since, both in the work plane and in the verification plane, the calibration device optionally is the last element in the beam path to the work plane and to the verification plane, respectively, and hence additional optical elements, which were not considered during the characterization of the laser beam, are not arranged in the beam path when the laser beam is applied to the processing object or the eye to be treated.

Some embodiments offer the advantage that the laser beam can be characterized objectively on the basis of a change in the thickness of the test object, consequently facilitating an objective characterization or assessment of the laser beam. This allows the characterization to be carried out more reliably than by way of a conventional characterization using a fluence paper, and consequently allows a particularly precise adjustment of the laser or laser beam which optionally is not influenced or falsified by subjective impressions.

Further, some embodiments offer the advantage that the characterization of the laser beam can be implemented in automated fashion and thus can be implemented independently by the laser or an apparatus related therewith. In particular, provision, impingement and/or evaluation (determination of the thickness) of the test object can be automated and thus unburden the operator. Particularly advantageously, a plurality of thickness changes as a result of material ablation can be determined for a plurality of impingements at one test site, and so forming the mean and/or statistical analysis can attain a high measure of certainty in or reliability of the laser beam characterization. According to an optional embodiment, the change in thickness is determined after each individual laser pulse of a pulse sequence.

Some embodiments further offer the advantage here that the automated characterization can also be implemented efficiently from economical points of view since the method according to some embodiments can be carried out more cost-effectively than the method known from the prior art that is based on the production of a lens profile and the subsequent verification of the lens profile.

Further, some embodiments offer the advantage that the method for characterization can already be integrated into laser equipment, for instance into excimer lasers, and/or into apparatuses for refractively correcting the cornea, by virtue of an apparatus for characterizing the laser beam being able to be implemented during planning and production. Alternatively, this offers the option of retrofitting and/or augmenting already existing excimer lasers and/or apparatuses for refractively correcting the cornea which do not comprise such an apparatus for characterizing the laser beam with an apparatus according to an optional embodiment.

Optionally, the aperture arrangement further comprises a third aperture of the plurality of apertures which has a predetermined extent along the scanning direction which is smaller than the mean diameter of the laser beam in the work plane and which is arranged at a predetermined distance from the first aperture along the scanning direction. The method optionally further comprises determining an alignment parameter of the laser processing system using the predetermined distance between the third aperture and the first aperture. This offers the advantage that it is also possible to characterize and/or check and/or calibrate the scanning movement and/or especially a deflection device used to bring about the scanning movement. In particular, this is facilitated by virtue of the laser beam being moved along the scanning direction in such a way that the latter sweeps over both the first and the third aperture, the laser beam optionally being moved directly and in a straight line from the first to the third aperture. However, the laser beam can be moved with jumps according to other embodiments such that, for example, the laser beam first sweeps over the first aperture, then jumps to the third aperture and sweeps over the latter, and subsequently jumps back to the second aperture and sweeps over the latter. As a result of the predetermined distance between the first and the third aperture it is subsequently possible to check whether the scanning movement is carried out as specified or whether there is a deviation between the target and actual movement. By way of example, the presence of a deviation may be an indication of a lack of calibration and/or scanner gain.

Optionally, the extent of the laser beam along the scanning direction is further determined on the basis of the determined energy of the laser beam transmitted through the third aperture. Particularly optionally, the determination of the extent of the laser beam along the scanning direction comprises the calculation of a mean of the extents of the laser beam determined on the basis of the first and the third aperture. This offers the advantage that a measurement error can optionally be reduced on account of a plurality of measurement values and the determination of the extent can therefore be implemented more reliably.

Optionally, the scanning of the laser beam is implemented in a first scan portion and in a second scan portion, the scanning direction in the first scan portion running along a first dimension parallel to the work plane and the scanning direction in the second scan portion running along a second dimension parallel to the work plane. This offers the advantage that the extent of the laser beam can be determined along a plurality of scanning directions. Particularly optionally, the scanning direction runs in such a way in the two scan portions that the extent of the laser beam can be determined in both dimensions of the work plane. Particularly optionally, the scanning direction in the first scan portion runs perpendicular to the scanning direction in the second scan portion.

Optionally, the first aperture has the predetermined extent along the scanning direction in the first scan portion. Moreover, the aperture arrangement optionally has an additional aperture of the plurality of apertures which has a predetermined extent along the scanning direction in the second scan portion, which is smaller than the mean diameter of the laser beam in the work plane. Expressed differently, the aperture arrangement has two apertures at a predetermined distance from one another and with a predetermined extent (along the scanning direction) for each scan portion or for each of the two scanning directions, and so two apertures are available for determining the extent in both scanning directions or along both scan portions. In this way, there can also be a calibration and/or characterization of the scanning movement in two dimensions.

Optionally, the apertures which have a predetermined extent along the scanning direction that is smaller than the mean diameter of the laser beam in the work plane have an extent that is no more than 90%, more optionally no more than 80%, even more optionally no more than 70%, yet more optionally no more than 60%, most optionally no more than 50% of the mean diameter of the laser beam in the work plane. Alternatively or in addition, the extent along the scanning direction is at least 1%, further optionally at least 5%, even more optionally at least 10%, yet more optionally at least 15%, most optionally 20% of the mean diameter of the laser beam in the work plane. By way of example, the laser beam in the work plane may have a mean diameter (FWHM) of approximately 0.6 mm to 0.8 mm, with larger or smaller diameters also being able to be used. The extent of the stop elements which have a predetermined, smaller extent along the scanning direction than the mean diameter of the laser beam may for example range between 0.1 mm and 0.4 mm along the scanning direction. The predetermined extents of a plurality of apertures with predetermined extents smaller than the mean diameter of the laser beam may, independently thereof, have identical extents or dimensions or different extents in each case.

Optionally, the plurality of apertures comprise at least two apertures for each scan portion, the at least two apertures having a predetermined extent along the respective scanning direction which is smaller than the mean diameter of the laser beam in the work plane and being arranged at a predetermined distance from one another along the respective scanning direction. This offers the advantage that both the extent and the diameter of the laser beam can be determined along each scan portion and, moreover, it is possible to implement a verification and/or calibration of the scanner movement or of the movement of the deflection device, that is to say for example of the deflection mirrors for moving the laser beam in the work plane, on the basis of the specified spacing of the apertures, for example by virtue of the two apertures being successively swept over in a contiguous straight-lined movement and the deflection and/or movement of the deflection mirrors required to this end being determined. Expressed differently, it may optionally be determined in this way whether the actually effected scanning movement corresponds to an expected target scanning movement. Should this not be the case, an adjustment and/or calibration of the deflection mirrors may be advantageous or even necessary.

Optionally, the laser beam is checked by means of the method, that is to say the method is used to check the work laser beam and optionally also a target laser beam of the laser processing system. The laser beam is optionally a laser beam used to carry out the laser processing of the processing object in the work plane. In this case, the laser beam may have a central wavelength which is invisible or only poorly visible to the human eye, for example in the ultraviolet or in the infrared spectral range, which may make an adjustment of the laser beam more difficult. Therefore, it may be advantageous to use a target laser beam for the adjustment of the laser processing system, the former optionally having a central wavelength in the visible spectral range. Optionally, the propagation directions of the laser beam and the target laser beam are coupled to one another in such a way that these propagate along the same optical axis and thus an adjustment of the laser processing system using the target laser beam also leads to an adjustment of the laser beam. This offers the advantage that coupling of the laser beam and the target laser beam can be checked in order to ensure the reliability of an adjustment of the laser processing system using the target laser.

Optionally, the aperture arrangement further comprises one or more target laser detectors in order to detect the target laser beam transmitted through an aperture and/or to determine its energy and/or power. In this case, the target laser detector or detectors may optionally be formed separately from the photodetector for detecting the laser beam. By way of example, the target laser detectors may have a different form to the photodetector. By way of example, the target laser detectors may optionally have a different design to the photodetector in terms of their sensor area and/or their spectral sensitivity. Particularly optionally, the photodetector is designed to detect the laser beam and is accordingly adapted to the wavelength in respect of the spectral sensitivity and adapted to the energy of the laser beam in respect of the destruction threshold, whereas the target laser detector or detectors are optionally adapted to the target laser beam in respect of the spectral sensitivity and the destruction thresholds.

Optionally, the method further comprises determining a fluence and/or an intensity of the laser beam in the work plane using the determined extent of the laser beam and the determined energy parameter of the laser beam. By way of example, to this end it may be advantageous to determine the extent of the laser beam in two dimensions of the work plane. Determining the fluence and/or the intensity offers the advantage that the parameter relevant to material ablation to be brought about, in particular for ophthalmic surgery, for instance the ablation of part of the cornea, is directly determined in this way and the ablation from the processing object, for example from the eye, to be expected can be anticipated particularly accurately.

Optionally the method comprises an adjustment of a laser parameter and a repeated implementation of steps b) to d) after the adjustment of the laser parameter. Expressed differently, the laser beam is optionally checked again after an optional adjustment of laser parameters or the laser beam has been implemented. This offers the advantage of being able to check success of the adjustment and being able to determine whether the implemented adjustment has obtained the desired success and/or whether a further adjustment of the laser beam or the laser processing system is recommended and/or advantageous and/or necessary.

Optionally, the aperture arrangement is designed to absorb and/or reflect some of the laser beam which has not been transmitted through the apertures. Optionally, the aperture arrangement is designed to transmit the laser beam only through the apertures. The aperture arrangement is optionally non-transmissive to the laser beam away from the apertures. In this case, the aperture arrangement is optionally designed such that the laser beam impinging on the aperture arrangement does not lead to any damage to and/or to destruction of the aperture arrangement which would impair the function of the aperture arrangement. By way of example, the aperture arrangement may be formed at least in part from a plastic and/or a metal. By way of example, the aperture arrangement may comprise an optionally black anodized metal in order to reduce the reflectivity of the aperture arrangement so as to avoid impairments and/or damage and/or a risk to humans as a result of a laser beam being reflected by the aperture arrangement. Alternatively the stop or the surface of the aperture arrangement may have a diffusive design and scatter incident light from the UV and/or visible and/or IR spectral range over a large solid angle. This may offer the advantage that at least one of the apertures, in particular a central aperture, can be identified as a pupil in an IR image by an eye tracker.

Optionally, the first aperture is in the form of a slot and the predetermined extent corresponds to a predetermined width of the slot. This offers the advantage that the aperture may have a very small and defined width along one dimension and may have a form that is larger than the mean diameter of the laser beam along the other dimension. As a result, the transmitted part of the laser beam is only restricted along one dimension, for example by virtue of a "strip" of the laser beam being transmitted, such that despite a defined width along the scanning direction a component of the laser beam that is as large as possible is transmitted along the other dimension perpendicular to the scanning direction in order to obtain the best possible signal-to-noise ratio. Optionally, the aperture arrangement has a plurality of slot-shaped apertures, which have a predetermined width which corresponds to the predetermined extent and which are respectively arranged in pairs at a predetermined distance from one another.

Optionally, the second aperture is in the form of a round hole and has an extent which substantially corresponds to the extent of the laser beam. The extent of the aperture substantially corresponding to the extent of the laser beam means that the laser beam can be substantially fully transmitted through the aperture, especially if the laser beam and the aperture are arranged concentrically. This means that the power or energy blocked or not transmitted by the second aperture is less than 0.5% of the overall power or overall energy. In this case, a round design of the aperture, for example as a round hole, may be particularly advantageous for fitting to the laser beam since the latter optionally likewise has a round cross-sectional form in the work plane.

Optionally, the stop and the photodetector are designed to be located parallel above one another. This offers the advantage that the aperture arrangement can have a particularly compact form and can accordingly be particularly suitable for arranging the aperture arrangement in the work plane. In this case, the aperture arrangement being arranged in the work plane optionally means that the stop and especially the apertures are arranged in the work plane.

Optionally, the laser processing system is configured to scan the laser beam over the aperture arrangement along a scanning direction parallel to the work plane by using the deflection device, in such a way that the laser beam at least sweeps partly over the apertures. Further, the laser processing system is configured to use the photodetector to determine an energy of the laser beam respectively transmitted through the apertures during the scanning procedure. Moreover, the laser processing system is further configured to determine an extent of the laser beam along the scanning direction on the basis of the determined energy of the laser beam transmitted through the first aperture and to determine an energy parameter of the laser beam on the basis of the determined energy of the laser beam transmitted through the second aperture.

Optionally, the laser processing system is designed as a laser treatment system for ophthalmic or refractive surgery on an eye, in particular for refractive corneal surgery.

Moreover, according to an optional embodiment, the aperture arrangement according to an embodiment can be used to characterize a laser beam of a laser processing apparatus in a work plane and in a verification plane (for example, internally within the laser processing system). Likewise, the method for characterization can be carried out in such a way that a calibration parameter is determined in the work plane and a verification parameter is determined in a verification plane.

Optionally, the method for characterizing a laser beam of a laser processing system is carried out in such a way that said method comprises the following steps:
  determining an energy parameter of the laser beam;
  providing a calibration device in a work plane of the laser processing system and having the laser beam impinge on the calibration device under the same conditions as are provided for the use of the laser beam for processing a processing object;
  determining a calibration parameter by means of the calibration device in the work plane;
  providing the calibration device in a verification plane outside of the work plane and deflecting the laser beam in such a way that the laser beam impinges on the calibration device in the verification plane;
  determining a verification parameter by means of the calibration device in the verification plane;
  determining a deviation factor which characterizes a deviation between the calibration parameter and the verification parameter;
  characterizing the laser beam by means of the calibration device in the verification plane using the energy parameter and the deviation factor.

In this case, the calibration device may comprise or be in the form of an aperture arrangement. Moreover, the determination of the calibration parameter and/or the verification parameter can be implemented in accordance with a method for characterizing a laser beam of a laser processing system.

Moreover, according to an optional embodiment, the laser processing system can be designed to carry out a characterization of the laser beam in the work plane and in the verification plane. To this end, the laser processing system may optionally comprise an energy sensor which is designed to determine an energy parameter of the laser beam. Further, the laser processing system in this case comprises a calibration device which has a choice of being arrangeable in a work plane of the laser processing system and being able to be impinged by the laser beam and of being arrangeable in a verification plane outside of the work plane and being able to be impinged by the laser beam, and a deflection element which is arrangeable in the beam path of the laser beam, in such a way that the deflection element deflects the laser beam, which is directed at the work plane, into the verification plane. In this case, the laser processing system is configured to arrange the calibration device in the work plane and determine a calibration parameter, to arrange the calibration device in the verification plane and determine a verification parameter, to determine a deviation factor which characterizes a deviation between the calibration parameter and the verification parameter, and to characterize the laser beam by means of the calibration device in the verification plane using the energy parameter and the deviation factor.

Optionally, the calibration device provided in the verification plane is a calibration device that is formed separately from the calibration device provided in the work plane. Expressed differently, two separate calibration devices are used or provided, in the control plane and in the work plane, in accordance with an optional embodiment. This offers the advantage that optionally the calibration device arranged in the verification plane may remain in its position and that it is only the calibration device provided in the work plane that needs to be moved from the work plane for the treatment of an eye or for the processing of a processing object. Optionally, the calibration devices may have a similar or even identical form.

According to another optional embodiment, the same calibration device is used both in the work plane and in the verification plane. This offers the advantage that only one calibration device need be provided. Further, this offers the advantage of being able to avoid deviations between the calibration parameter and the verification parameter on account of deviations between the two separate calibration devices.

Optionally, the verification parameter is determined temporally directly after the determination of the calibration parameter. This offers the advantage of being able to minimize deviations on account of temporal variations in the laser processing system.

Optionally, the energy parameter is determined at least during the determination of the calibration parameter and during the determination of the verification parameter. Particularly optionally, the energy parameter is determined continuously. This offers the advantage that changes emerging from a deviation in the energy of the laser beam are able to be identified and are able to be considered when comparing the calibration parameter with the verification parameter.

Optionally, the laser beam is only deflected by means of exactly one optical deflection element. Expressed differently, a change in the beam path of the laser beam for the purposes of the deflection from the work plane to the verification plane is implemented only by means of the deflection element. This offers the advantage of reducing to a minimum bothersome influences on the laser beam, which may lead to a deviation between the laser beam provided in the work plane and the laser beam provided in the verification plane. Particularly optionally, the deflection element can be monitored and/or checked regularly, for example by virtue of determining a reflectivity and/or transmissivity of the deflection element. By way of example, the laser beam and/or any other optical radiation can be used for this purpose.

Optionally, the laser processing system is designed to automatically alternate the arrangement of the calibration device between the work plane and the verification plane and/or to automatically introduce the deflection element into the beam path of the laser beam and/or remove said deflection element from the beam path. This offers the advantage that only one calibration device is required and, optionally, a calibration and/or a characterization of the laser beam may be carried out completely automatically.

Optionally, the calibration device is designed to provide a measurement value which scales linearly with laser energy. By way of example, the calibration device may have an aperture arrangement with a stop and a photodetector, by means of which the fluence and/or the intensity of the laser beam can be determined by virtue of the fact that the laser beam is scanned over one or more apertures of the stop. In this case, it may be advantageous if the measurement signal of the photodetector has a linear relationship with energy and/or fluence of the laser beam.

Optionally, the laser beam is deflected into the verification plane by means of a deflection element which is brought into the beam path for this purpose. By way of example, the deflection element can be in the form of a mirror. According to another embodiment, the deflection element may also remain in the beam path and a change in its orientation may achieve a deflection of the laser beam into the verification plane.

Optionally, the laser processing system is designed to independently move the calibration device or the aperture arrangement between the work plane and the verification plane, for example by means of an appropriate translating and/or pivoting apparatus. By way of example, this change in position is brought about in such a way that the optical path of the laser beam to the work plane and to the verification plane has the same length.

Optionally, the method comprises a functionality test of the photodetector in order to check its functioning. By way of example, such a functionality test can be implemented on the basis of secondary effects of an interaction between the laser beam and the detector, for instance using an arising fluorescence and/or temperature, and/or mechanical shockwaves and/or acoustic waves.

According to an optional embodiment, the aperture arrangement has two first apertures, which are in the form of a slot and run parallel to one another. In this case, the width of the slot-shaped first apertures is smaller than the extent of the laser beam in the work plane such that the energy of the laser beam transmitted through the respective aperture can be determined on the basis of the laser beam sweeping over the first apertures and such that an extent of the laser beam in the work plane can be determined therefrom. Additionally, the two slot-shaped first apertures are arranged at a predetermined distance from one another, optionally in a direction perpendicular to the longitudinal direction of the slot-shaped apertures. Moreover, on the basis of sequentially sweeping over the two first apertures perpendicular to the longitudinal direction of the slots in one movement, it is possible to calibrate the scanner or the deflection device of the laser processing system. Moreover, the aperture arrangement according to this optional embodiment has a further aperture which is in the form of a round hole, for example, and which has such a shape and size that the laser beam is substantially fully transmitted through the second aperture when the laser beam passes through the second aperture so that the energy or power of the laser beam can be determined by means of the second aperture. In this case, the photodetector is arranged in such a way that the part of the laser beam transmitted through the respective apertures is incident on the photodetector and can be determined by the latter. Optionally, the second aperture is arranged between the two first apertures. As a result, by way of a single straight-lined scanning movement, the laser beam can be guided in such a way that the latter initially sweeps over the first slot-shaped aperture, then sweeps over the second (round hole-shaped) aperture and subsequently sweeps over the second slot-shaped aperture such that a single scanning movement allows determination of the extent of the laser beam (at the first slot-shaped aperture), determination of the energy of the laser beam (at the second round hole-shaped aperture) and calibration of the scanner (on the basis of the movement over the two slot-shaped apertures). The fluence or target fluence of the laser beam in the work plane can be determined by means of the determined size and energy of the laser beam. Thus, this embodiment offers the option of carrying out the determination of the fluence and the calibration of the scanner in a single procedure.

According to a further optional embodiment, the aperture has a slot-shaped aperture, the width of which is smaller than the extent of the laser beam in the work plane, and a round hole-shaped aperture, which is larger than the extent of the laser beam in the work plane, for determining the fluence of the laser beam in the work plane. In this case, these apertures are arranged so as to overlap with a photodetector in order to determine the energy of the laser beam and the fluence. Further, the aperture arrangement according to this embodiment has a further slot-shaped aperture which overlaps with a target laser detector and which can be used to implement referencing between the target laser beam and the laser beam. This embodiment offers the advantage that determining the fluence of the laser beam and referencing the laser beam with the target laser beam can be implemented in one procedure in the work plane.

According to an optional embodiment, the method further comprises a determination of a target fluence. In this context, the target fluence is a sought-after target value of the fluence which should be used for the processing by means of the laser processing system. In this case, the target fluence may depend on the focus size or spot size of the laser beam in the work plane. By way of example, the method may comprise a determination of an (actual) fluence, that is to say an actual value of the fluence, and a determination of the focal size or the extent of the laser beam in the work plane. Provided the fluence is outside of a tolerance range, a readjustment or calibration of the laser processing system, for example, may be undertaken or proposed, this for example comprising a change in the power and/or energy of the laser beam in order to obtain the desired target fluence.

By way of example, the optional determination of the target fluence can be implemented in such a way that the beam diameter d of the laser beam in the work plane is determined first. From this (and further known relationships), a target fluence is subsequently calculated. Further, the energy of the laser beam is measured. The current fluence of the laser beam in the work plane is determined from the energy and diameter d. It is compared with the target fluence. In the case of deviations, a laser parameter (usually the energy of the laser beam), for example, is adjusted so that the actual fluence and the target fluence correspond sufficiently well, that is to say until the difference drops below a predetermined tolerance threshold. Accordingly, the target fluence itself may optionally be a variable in this process, which depends on the parameter of the beam diameter or extent of the laser beam in the work plane.

Therefore, the target fluence may offer a large amount of information since an ablation calibration has optionally been taken into account when calculating the target fluence from the beam diameter (that is to say, a specification in respect of "the amount of volume of PMMA or cornea ablated for a given beam size and energy"). Optionally, this information is obtained independently of the method described herein and is determined in advance so that a correct ablation can be ensured by means of the fluence calibration.

By way of example, exemplary values for the target fluence (Ftarget) in the case of a beam diameter of 700 μm and 600 μm, respectively, might be:

$F\text{target}(700\ \mu m) = 190\ mJ/cm^2$ $F\text{target}(600\ \mu m) = 240\ mJ/cm^2$ Typically, the target fluence varies nonlinearly with the beam diameter.

The optional determination of the target fluence offers a certain amount of flexibility with (slowly) varying diameters (e.g., in the case of drifts in imaging systems) in order to nevertheless be able to calibrate the ablation well, since the beam diameter and the laser energy are considered in full.

The steps for the optional determination of the target fluence according to an optional embodiment are specified below in exemplary fashion:
1) determining the extent of the laser beam (spot size d) and the energy E of the laser beam in the work plane;
2) calculating the fluence present (actual fluence) on the basis of the extent of the laser beam (d) and the energy E;
3) calculating the target fluence from the extent of the laser beam (d) and a predetermined transformation;
4) comparing the actual fluence with the target fluence and determining a possible deviation;
5) checking, on the basis of the possible deviation, whether it is necessary to calibrate the laser processing system, and optionally carrying out the calibration.

The optional configurations explained below relate, in particular, to the optional embodiments which comprise having the laser beam impinge on a test object and determining a change in the thickness of the test object at the test site on account of the laser beam impinging thereon. These may optionally be combined with other methods for characterizing the laser beam.

According to an optional embodiment, the determination of the change in the thickness of the test object at the test site comprises a measurement of the thickness of the test object at the test site after the laser beam has impinged thereon and a comparison of the determined thickness with the thickness of the test object at the test site before the laser beam impinged thereon. By way of example, the thickness of the test object at the test site may be known in advance and stored in the system such that there can be a comparison of the determined thickness following the impingement with the thickness prior to the impingement known in advance. Optionally, this comparison can be realized by forming a mathematical difference between and/or mathematical ratio of the determined thicknesses. The comparison can then optionally be used to enable subsequent laser material processing, for example on a human cornea, and/or to configure the laser material processing or the material ablation, for example in respect of optimal processing parameters, for instance laser pulse energies and/or number of laser pulses, laser spot sizes and/or scanning patterns.

To obtain a desired accuracy of the determination of the thickness or change in thickness of, for instance, between 100 nm and 1 μm, this optional embodiment however requires the thickness of the test object to be known with a correspondingly high accuracy before the laser beam impinges thereon.

According to an optional embodiment, the determination of a change in the thickness of the test object at the test site further comprises a measurement of the thickness of the test object at the test site before the laser beam impinges thereon. According to such an optional embodiment, the thickness of the test object before the laser beam impinges thereon can be determined in addition to the determination of the thickness of the test object after the laser beam has impinged thereon. This offers the advantage of being able to particularly reliably determine the change in the thickness on account of the laser beam impingement. Moreover, this facilitates the use of test objects with an unknown thickness and/or with a thickness whose specification is not within the desired accuracy range, and/or of test objects with a pronounced surface roughness relative to the desired accuracy, as a result of which the costs associated with providing the test objects can be lowered and the characterization of the laser beam can be implemented in a particularly cost-effective manner.

According to an optional embodiment, the method further comprises a configuration of the laser beam for ongoing and/or subsequent material processing by means of the laser beam on the basis of the determined change in the thickness of the test object at the test site on account of the laser beam impinging thereon. Expressed differently, there optionally is a configuration and/or an adjustment of parameters of the laser beam and/or other parameters of material ablation by means of the laser beam on the basis of the implemented characterization of the laser beam. Particularly optionally there is a regular characterization of the laser beam and a possible adjustment of parameters of the laser beam and/or the material ablation method on the basis of the characterization. If necessary, the characterization of the laser beam may also require an interruption and/or termination of the material ablation by means of the laser beam, or may make this appear advantageous. Alternatively or in addition, the laser beam may be adjusted automatically and/or a notification may be output to the user that an adjustment of the laser beam and/or of the apparatus for material ablation may be advantageous or required.

According to an optional embodiment, the determination of the change in the thickness of the test object at the test site is implemented by means of an optical measurement of the thickness. This offers the advantage that the determination can be implemented particularly quickly and/or sensitively. Moreover, this offers advantages for reliable automation of the determination and the evaluation of the determined thicknesses.

According to an optional embodiment, the optical measurement comprises radiating optical radiation into the test object from a side of the test object that faces away from the direction of incidence of the laser beam. Moreover, the optical measurement optionally comprises a detection of a reflection and/or a scattering of the optical radiation at and/or in the test site of the test object. Expressed differently, the laser beam can impinge on the test object on a first side of the test object while the optical radiation for determining the thickness of the test object is radiated onto the opposite side of the test object. Thereupon, the thickness of the test object at the test site can be determined or measured on the basis of a reflection and/or scattering of the optical radiation radiated-in, on the surface of the test object which is and/or was exposed to the laser beam impinging thereon. This offers the advantage that the optical measurement can be carried out with a particularly simple and/or compact measurement structure.

According to an optional embodiment, the optical measurement comprises a measurement of the thickness of the test object at the test site by means of at least one confocal-chromatic sensor. This facilitates a particularly precise and quick measurement of the thickness of the test object. Moreover, the use of one or more confocal-chromatic sensors facilitates a reliable automation of the optical measurement and the evaluation of the measurement results for characterizing the laser beam. By way of example, confocal-chromatic sensors may be used to this end, as are commercially available from MIKRO EPSILON. Such confocal-chromatic sensors offer the advantage that a wide range thereof are available in relation to the size of the measurement field and the obtainable measurement accuracy, and consequently the confocal-chromatic sensors can be adapted to the respective requirements in this respect or can be chosen accordingly. In particular, confocal-chromatic sensors with a measurement accuracy of up to 10 nm are available, and so during the characterization of the laser beam these sensors are able to obtain the accuracy required for the refractive correction of the cornea.

According to an optional embodiment, the laser beam is provided as a pulsed laser beam, the laser beam impinging on the test object optionally being implemented in such a way that a single laser pulse sequence or a pulse sequence or a number or plurality of laser pulses with a certain number of laser pulses ablates the portion of the material of the test object at the test site of the test object. Optionally, a further laser pulse sequence in each case impinges on the test object at other test sites. This offers the advantage that the characterization of the laser beam can be implemented particularly accurately since the amount of impinged energy can be specified particularly accurately on the basis of the number of laser pulses.

According to an optional embodiment, the laser pulse sequences with different energies impinge on the various test sites. This facilitates a particularly precise characterization on the basis of a comparison of the thickness of the various test sites.

According to an optional embodiment, the test object is formed at least in part from PMMA. Optionally, the test object is dimensioned such that one or more test sites can be arranged on the test object. By way of example, the test object can be substantially larger than a single test site. By way of example, the test object can be displaced relative to the laser beam in a direction and/or plane perpendicular to the propagation direction of the laser beam and/or the laser beam can be moved relative to the test object, in order for the laser beam to impinge on a different site on the test object. According to an optional embodiment, the test object can for example be rotated perpendicular to the propagation direction or optical axis of the laser beam in order to provide a separate test site for each pulse and/or each predetermined series of laser pulses or each pulse sequence. This offers the advantage of being able to use the test object multiple times and accordingly reducing the requirement of changing the test object and/or reducing the frequency of the change. Consequently, this offers the advantage that the maintenance works can be reduced. For an optional multiple use of the test object, in particular between a plurality of instances of corneal processing, it is advantageous that the laser beam is intermittently deflected out of the processing zone of the cornea and deflected to a test object situated at another site, for example by means of a folding mirror, or else that the test object can be folded in and/or retracted optionally in motor-driven fashion between treatments in the usual corneal treatment region. In this case, the deviation of the positions of the laser focus on the cornea and on the test object surface should optionally be designed to be small in order to keep the processing conditions similar, for example so that the laser spot sizes optionally deviate from one another by less than a factor of 2.

According to an optional embodiment of an optional embodiment, the apparatus can be designed such that at least some of the test object can be scanned and the thickness is ascertained at at least one test site in the process, by means of a relative movement, at least partly perpendicular to the optical axis, between the test object and the at least one confocal-chromatic sensor. By way of example, the relative movement can be obtained by moving the at least one confocal-chromatic sensor and/or the test object. By bringing about a relative movement and scanning at least some of the test object it is possible to significantly increase the examinable area. Additionally, what can optionally be obtained thereby is that the thickness in different ablation zones or test sites is determined using the same confocal-chromatic sensor, different shot numbers or laser pulse numbers and/or a different radiation energy, for example, having impinged on the various test sites or ablation zones. This may be advantageous for determining the material ablation per laser pulse or shot.

According to a further optional embodiment, the optical axis of the laser beam is superimposed on the optical axis of the confocal-chromatic sensor, for example by means of a beam splitter. What this can optionally achieve is that the material ablation by each individual shot or laser pulse can be determined, even when processing the cornea of a human eye. In this embodiment, it may be advantageous to arrange the confocal-chromatic sensor on the same side of the test object or the cornea from which the laser beam is also incident.

According to an optional embodiment, the apparatus for characterizing the laser beam can be integrated in a laser system. In this case, the apparatus may optionally have a device for automatically providing a test object. By way of example, a plurality of test objects may be kept available in the apparatus and/or in the laser system, said test objects then being provided and used when required for the characterization of the laser beam. Further, the apparatus and/or the laser system may have a maintenance shaft for example, from which used test objects can be taken and/or into which unused test objects can be reloaded, for example. By way of example, one or more test object may also be designed in the form of a foil band and/or in the form of an adjustable and/or rotatable plastic disk, which offer a plurality of suitable areas for test sites by a displacement and/or a rotation perpendicular to the optical axis of the laser beam. By way of example, the plastic disk may be formed like a CD. This may reduce the servicing outlay for replacing the test objects. Optionally, several thousand processes for characterizing the laser beam are facilitated in this way, before the test object or objects need to be replaced.

According to an optional embodiment, the method for characterizing a laser beam of a laser processing system may further comprise a determination of an energy parameter of the laser beam. Moreover, the method may include providing a calibration device in a work plane of the laser processing system and having the laser beam impinge on the calibration device under the same conditions as are provided for the use of the laser beam for processing a processing object, and determining a calibration parameter by means of the calibration device in the work plane. Further, the method may include providing the calibration device in a verification plane outside of the work plane and deflecting the laser beam in such a way that the laser beam impinges on the calibration device in the verification plane, and determining a verification parameter by means of the calibration device in the verification plane. Moreover, the method according to the optional embodiment comprises determining a deviation factor which characterizes a deviation between the calibration parameter and the verification parameter, and characterizing the laser beam by means of the calibration device in the verification plane using the energy parameter and the deviation factor.

Further, an apparatus for refractive correction of the cornea according to an optional embodiment comprises, or is in the form of, a laser processing system for processing a processing object by means of a laser beam. In this case, the laser processing system comprises an energy sensor which is designed to determine an energy parameter of the laser beam. Further, the laser processing system in this case comprises a calibration device which has a choice of being arrangeable in a work plane of the laser processing system and being able to be impinged by the laser beam and of being arrangeable in a verification plane outside of the work plane and being able to be impinged by the laser beam, and a deflection element which is arrangeable in the beam path of the laser beam, in such a way that the deflection element deflects the laser beam, which is directed at the work plane, into the verification plane. In this case, the laser processing system is configured to arrange the calibration device in the work plane and determine a calibration parameter, to arrange the calibration device in the verification plane and determine a verification parameter, to determine a deviation factor which characterizes a deviation between the calibration parameter and the verification parameter, and to characterize the laser beam by means of the calibration device in the verification plane using the energy parameter and the deviation factor.

In this case, the calibration device is optionally in the form of, or comprises, an apparatus for characterizing a laser beam according to an optional embodiment. In particular, a calibration device comprises a test object holder and a measuring device, a test object being provided in the test object holder for the purposes of characterizing the laser beam.

The method for characterizing a laser beam of a laser processing apparatus or of an apparatus for refractive correction of the cornea according to an optional embodiment can therefore optionally be carried out both in the work plane and in the verification plane, optionally internally within the laser processing system.

According to an optional embodiment, the calibration device provided in the verification plane is a calibration device that is formed separately from the calibration device provided in the work plane. Expressed differently, two separate calibration devices are used or provided, in the control plane and in the work plane, in accordance with an optional embodiment. This offers the advantage that optionally the calibration device arranged in the verification plane may remain in its position and that it is only the calibration device provided in the work plane that needs to be moved from the work plane for the treatment of an eye or for the processing of a processing object. Optionally, the calibration devices may have a similar or even identical form.

According to another optional embodiment, the same calibration device is used both in the work plane and in the verification plane. This offers the advantage that only one calibration device need be provided. Further, this offers the advantage of being able to avoid deviations between the calibration parameter and the verification parameter on account of deviations between the two separate calibration devices.

Optionally, the verification parameter is determined temporally directly after the determination of the calibration parameter. This offers the advantage of being able to minimize deviations on account of temporal variations in the laser processing system.

Optionally, the energy parameter is determined at least during the determination of the calibration parameter and during the determination of the verification parameter. Particularly optionally, the energy parameter is determined continuously. This offers the advantage that changes emerging from a deviation in the energy of the laser beam are able to be identified and are able to be considered when comparing the calibration parameter with the verification parameter.

Optionally, the laser beam is only deflected by means of exactly one optical deflection element. Expressed differently, a change in the beam path of the laser beam for the purposes of the deflection from the work plane to the verification plane is implemented only by means of the deflection element. This offers the advantage of reducing to a minimum bothersome influences on the laser beam, which may lead to a deviation between the laser beam provided in the work plane and the laser beam provided in the verification plane. Particularly optionally, the deflection element can be monitored and/or checked regularly, for example by virtue of determining a reflectivity and/or transmissivity of the deflection element. By way of example, the laser beam and/or any other optical radiation can be used for this purpose.

Optionally, the laser processing system is designed to automatically alternate the arrangement of the calibration device between the work plane and the verification plane and/or to automatically introduce the deflection element into the beam path of the laser beam and/or remove said deflection element from the beam path. This offers the advantage that only one calibration device is required and, optionally, a calibration and/or characterization of the laser beam may be carried out completely automatically.

Optionally, the calibration device is designed to provide a measurement value which scales linearly with laser energy. By way of example, the calibration device may be configured to determine material ablation and/or a change in a thickness of a test object on account of the laser beam impinging thereon, the material ablation and/or the change in the thickness optionally scaling linearly with the energy of the laser beam. Alternatively, the calibration device may have an aperture arrangement with a stop and a photodetector, by means of which the fluence and/or the intensity of the laser beam can be determined by virtue of the fact that the laser beam is scanned over one or more apertures of the stop. In this case, it may be advantageous if the measurement signal of the photodetector has a linear relationship with energy of the laser beam.

Optionally, the laser beam is deflected into the verification plane by means of a deflection element which is brought into the beam path for this purpose. By way of example, the deflection element can be in the form of a mirror. According to another embodiment, the deflection element may also remain in the beam path and a change in its orientation may achieve a deflection of the laser beam into the verification plane.

Optionally, the laser processing system is designed to independently move the calibration device between the work plane and the verification plane, for example by means of an appropriate translating and/or pivoting apparatus. By way of example, this change in position is brought about in such a way that the optical path of the laser beam to the work plane and to the verification plane has the same length.

It is understood that not only should the aforementioned features and embodiments and features and embodiments explained below be considered disclosed in the respective explicitly mentioned combinations but that other technically expedient combinations and embodiments are also comprised by the disclosure.

Further details and advantages of optional embodiments should now be explained in more detail on the basis of the following examples and optional embodiments with reference being made to the figures, in which.

The same or similar elements in the various embodiments are denoted by the same reference signs in the following figures for reasons of simplicity.

Figure 1A:
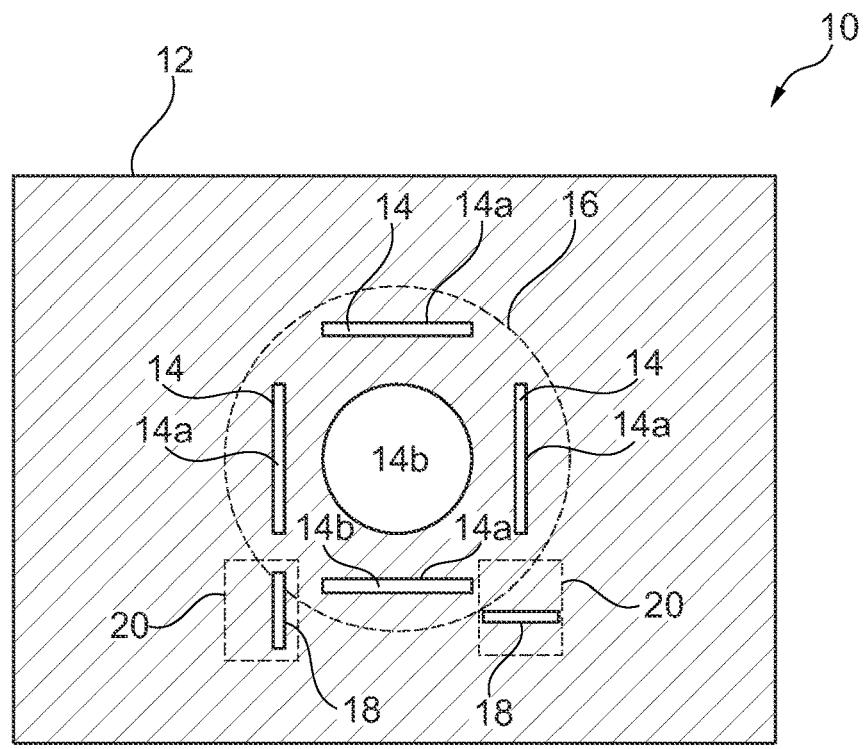
FIG. 1A to 1D show schematic illustrations of stop arrangements according to optional embodiments.

FIG. 1A shows, in plan view, a schematic illustration of an aperture arrangement 10 according to an optional embodiment. In particular, a stop 12 of the aperture arrangement 10, in which a plurality of apertures 14 have been formed, can be identified in the plan view. The apertures 14 include in particular slot-like apertures 14a, which are respectively formed in pairs at a predetermined distance 100a or 100b from one another and which each have a predetermined width. According to the illustrated embodiment, the apertures 14a respectively have the same thickness and the distances 100a and 100b are also dimensioned to be the same. However, this may be different according to other embodiments.

Further, the aperture arrangement 10 has a further aperture 14b, which is in the form of a round hole and which is arranged centrally in the stop 12 in accordance with the embodiment shown. The slot-like apertures 14a are arranged around the central, round aperture 14b.

A photodetector 16 whose detector area 16 overlaps with the apertures 14 is arranged below the stop 12 (and therefore not identifiable in FIG. 1A). According to the embodiment shown, the photodetector 16 has a round detector area, the circumferential boundary of which is indicated by the dashed line. The photodetector 16 is designed to detect a laser beam, that is to say a work laser beam, and to determine the energy radiated onto the photodetector by the laser beam. The photodetector 16 is therefore designed for the wavelength of the laser beam. If use is made of a laser beam with a wavelength in the ultraviolet spectral range, the photodetector 16 is optionally also designed for the ultraviolet spectral range or the corresponding wavelength of the work beam. A rasterization of the photodetector 16, that is to say a pixelation, is not mandatory in this case but possible by all means. Rather, it is sufficient for the energy of the laser beam transmitted through an aperture or the apertures 14 to be able to be detected by means of the photodetector and for the energy to be able to be determined.

The photodetector 16 and the aperture 12 are arranged over one another in this case such that all apertures 14 overlap with the photodetector 16. The energy transmitted through each of the apertures 14 when the laser beam sweeps over the respective aperture 14 is incident on the photodetector 16 and can be detected by the latter.

Moreover, the aperture arrangement 10 according to the shown embodiment has two further apertures 18 for the target laser beam, which likewise are in the form of a slot with a predetermined extent or width and which are arranged at the predetermined distance 100a from one another. Since the target laser beam typically has a different central wavelength to the work laser beam and therefore the photodetector 16 might not be designed to detect the target laser beam and/or determine the energy and/or power thereof, a separate target laser detector 20 is assigned to each aperture 18, each target laser detector being arranged below the associated aperture 18, as indicated on the basis of the dashed line. One of the two apertures 18 runs in the vertical direction and has a predetermined width in the horizontal direction whereas the other aperture 18 runs in the horizontal direction and has a predetermined width in the vertical direction. As a result, it is possible to determine the extent of the target laser beam in the work plane in both dimensions, referred to as horizontal and vertical in the present case.

As a result, the aperture arrangement allows both the laser beam and the target laser beam to be checked, even if these have entirely different central wavelengths.

In this case, the aperture arrangement 10 is dimensioned and formed in such a way that it can be arranged in the work plane of a laser processing system. In particular, it is therefore advantageous to choose the dimensions of the aperture arrangement 10 in such a way that positioning in possibly tight conditions is possible at the location of the work plane.

Figure 1B:
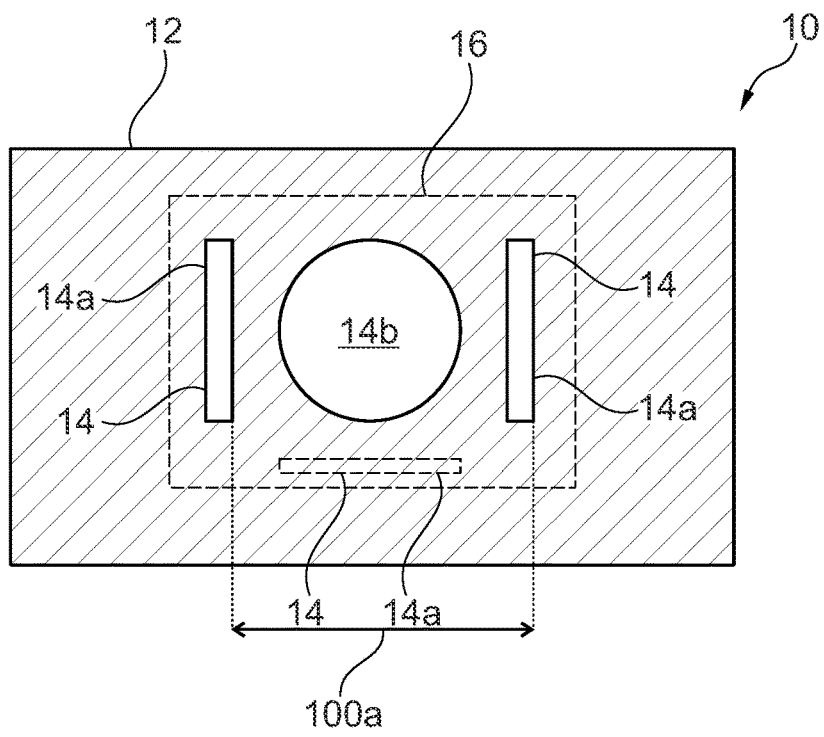

FIG. 1B shows an aperture arrangement 10 according to a further optional embodiment. The aperture arrangement according to this optional embodiment has two slot-like or slot-shaped apertures 14a, which are arranged so as to run parallel to one another at a predetermined distance 100a from one another. In this case, the apertures 14a have a width that is significantly smaller than the mean diameter or the mean extent of the laser beam in the work plane. Moreover, the aperture arrangement 10 has a further aperture 14b, which is in the form of a round hole and which is larger than the laser beam in the work plane such that the laser beam can be transmitted substantially fully through the round hole-shaped aperture 14b. Further, the aperture arrangement 10 has a photodetector 16 which is arranged below the stop 12, the photodetector being able to register and detect the laser radiation of the laser beam passing through the aperture.

This stop arrangement 10 allows determination of the fluence of the laser beam in the work plane and a calibration of the scanner in one procedure. By way of example, this can be implemented by scanning the laser beam in a straight-lined movement over the aperture arrangement starting from the left, so that the laser beam initially sweeps over the left slot-like aperture 14a (sweeping over said aperture in a manner perpendicular to its longitudinal axis), then passes centrally through the round hole-shaped aperture 14b and subsequently also sweeps over the right slot-shaped aperture 14a. A scan of the laser beam in the opposite direction, that is to say from right to left, is equally suitable. The size or extent of the laser beam in the work plane can be determined on the basis of the first and/or second slot-like aperture 14a being swept over by the laser beam. The energy or power of the laser beam can be determined on the basis of the laser beam that passes centrally through the round hole-shaped aperture 14b, so that the fluence in the work plane can be determined from the determined information. Moreover, the scanner movement can be calibrated on the basis of the movement over the two slot-like apertures 14a, and so the laser beam can be characterized and the scanner can be calibrated in one procedure.

Optionally, the aperture arrangement may additionally have two further slot-like apertures 14a, which are arranged (shown using dashed lines) perpendicular to the other two slot-like apertures 14a. This can be used to determine the extent of the laser beam in the work plane along the other dimension (vertical in the figure) and also calibrate a scanner movement in this direction.

Figure 1C:
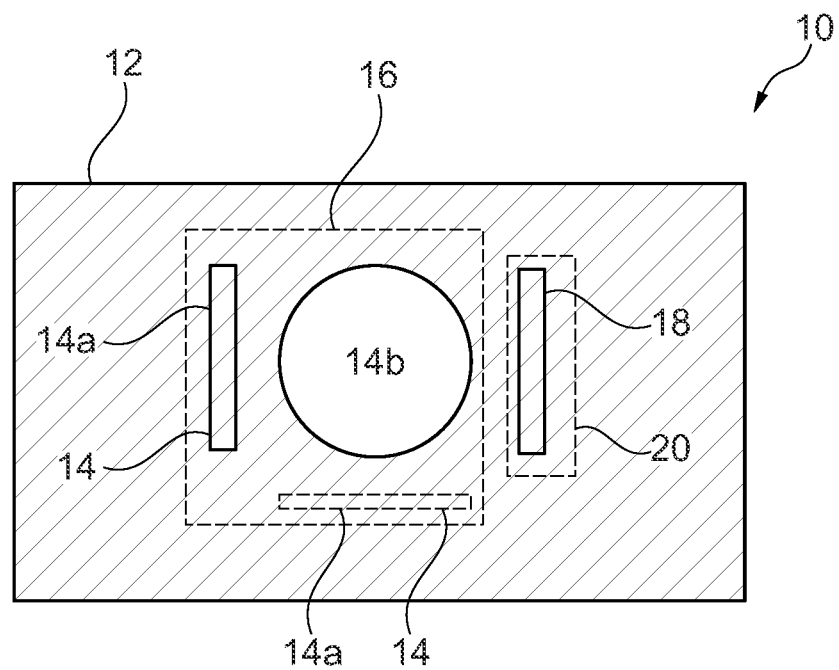

FIG. 1C shows an aperture arrangement 10 according to a further embodiment, which largely corresponds to the embodiment shown in FIG. 1B but deviates from the latter in the fact that only one vertically extending, slot-like aperture 14a is formed for the determination of the extent of the laser beam and, instead, a further vertically extending, slot-like aperture 18 is formed for determining the extent of the target laser. The slot-like aperture 18 accordingly also overlaps with a target laser detector 20 such that the radiation of this target laser beam passing through the aperture 18 can be detected and the extent of the target laser beam in the work plane can be determined. This embodiment facilitates a characterization of the fluence of the laser beam and a referencing of the target laser beam with the laser beam in the work plane in one procedure.

Figure 1D:
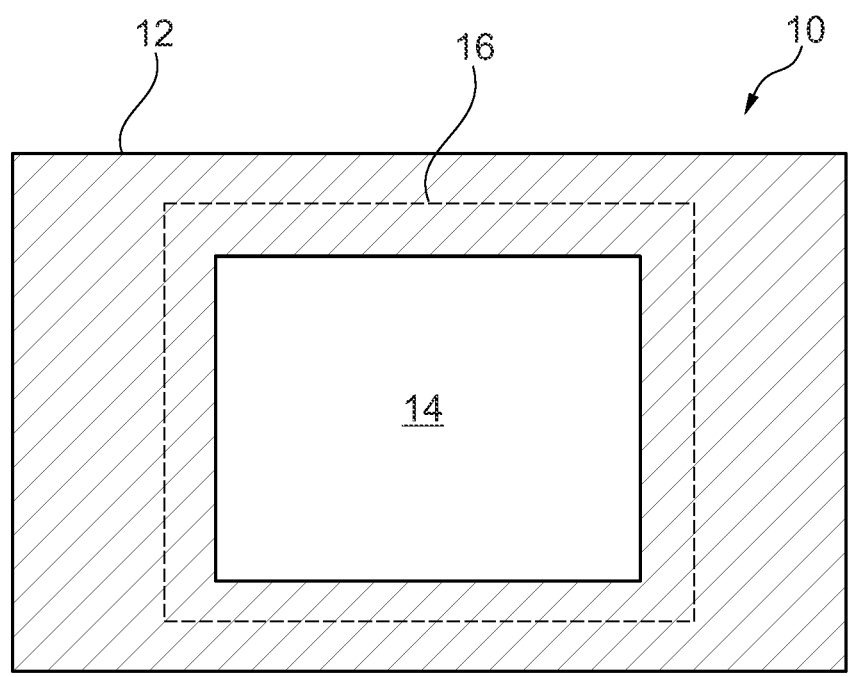

FIG. 1D shows a further optional embodiment of an aperture arrangement 10 which is distinguished in particular by its simplicity. The aperture arrangement 10 has only a single aperture 14, which is in the form of a rectangular hole with predetermined dimensions. Like in the case of the other embodiments as well, a photodetector 16 is arranged below the aperture 14 or the stop 12, the light of the laser beam passing through the aperture striking said photodetector. In particular, the aperture 14 is characterized in that it has two opposing, parallel edges that optionally extend in a straight line. By way of example, using an aperture arrangement 10 according to this embodiment, the laser beam can be characterized by virtue of the laser beam being guided in a straight-lined scanning movement over the aperture arrangement 10 in the work plane, in such a way that the laser beam sweeps over the aperture 14. In this case, sweeping is optionally implemented in such a way that the movement of the laser beam during the scan is implemented in perpendicular fashion over two opposing edges of the aperture 14. By way of example, such a scanning movement can be horizontal or vertical in the shown aperture. On the basis of sweeping over the edges of the aperture 14, it is possible firstly to determine the extent of the laser beam in the work plane and secondly to calibrate the scanner (on the basis of the predetermined spacing of the edges). In this case, the aperture 14 is dimensioned such that the laser beam is substantially fully transmitted when the latter passes through the aperture 14 in centered fashion. In this way, it is also possible to determine the energy or power of the laser beam by means of the photodetector 16. Consequently, the fluence of the laser beam in the work plane can be determined and the scanner can be calibrated in the same procedure even when an aperture according to this embodiment is used.

If moreover a target laser beam should be used, a further stop 18 with a photodetector 20 arranged therebelow is optionally also possible here, in order to calibrate processing laser beam and target laser beam with respect to one another, as already described above.

Figure 2A:
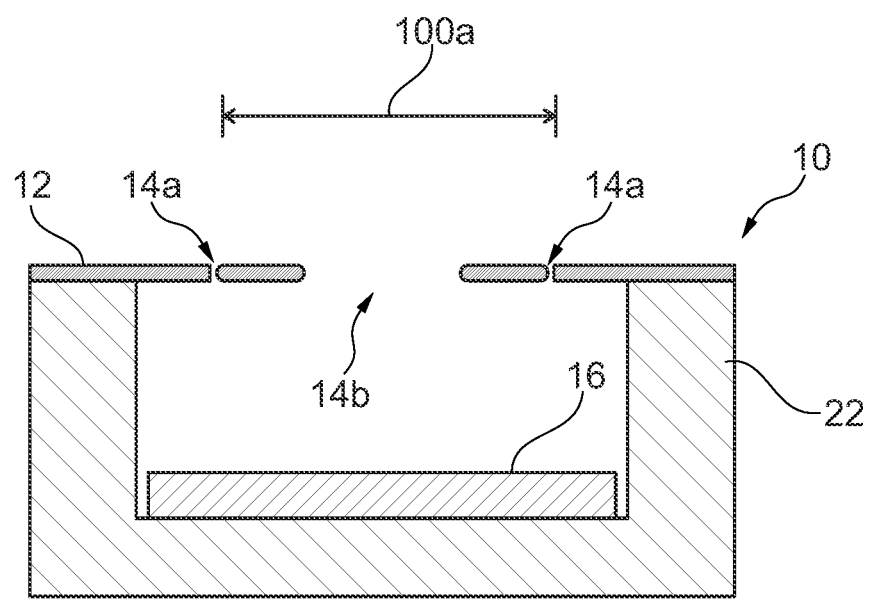
FIGS. 2A and 2B show two cross-sectional views of an aperture arrangement according to an optional embodiment.

FIG. 2A shows the aperture arrangement 10 according to an optional embodiment in a schematic cross-sectional view along a cross-sectional line A-A', as shown in FIG. 1. In this context, the aperture arrangement identifiably has a carrier element 22, on which the stop 12 is arranged lying on top. The carrier element 22 supports the stop 12 in the peripheral regions and forms a cavity within the carrier element 22 below the stop 12. The photodetector 16 is arranged in the cavity below the stop 12, in such a way that the photodetector or the detector area overlaps with the apertures 14a and 14b located thereover. If the laser beam sweeps over one of the apertures 14a and 14b, at least some of the energy of the laser beam is transmitted through the respective aperture 14a, 14b and is incident on the photodetector 16 located therebelow. In this context, the stop 14b is chosen in such a way in respect of shape and size that the laser beam can be substantially fully transmitted. The apertures 14a are significantly smaller than the mean diameter of the laser beam along the direction running horizontally in FIG. 2A, and so the size of the laser beam can be determined by means of sweeping over the respective aperture 14a.

Figure 2B:
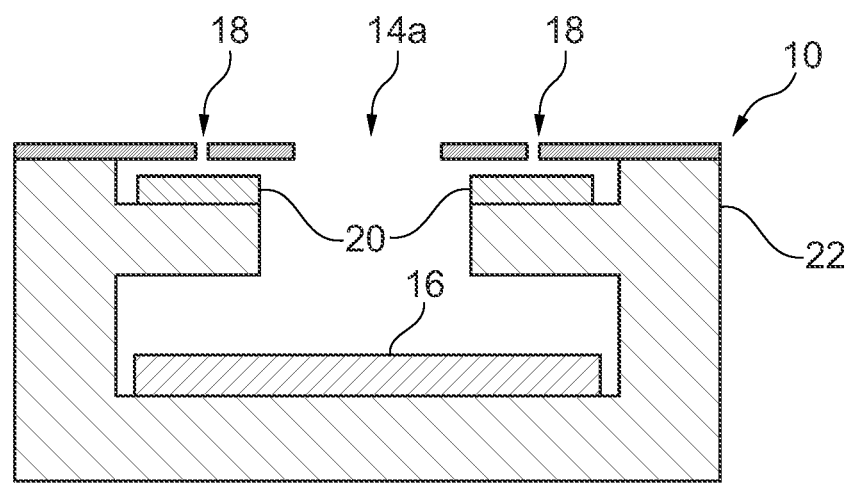

FIG. 2B shows a further schematic cross-sectional view along a section line B-B', as shown in FIG. 1. This cross section cuts the apertures 18 transversely and an aperture 14a longitudinally. Here, it is identifiable that a target laser detector 20 is arranged below the apertures 18 on each corresponding cantilever of the support element 22 such that some of the target laser beam is incident on the target laser detector 20 when sweeping over the respective aperture 18 and can be detected by said target laser detector. According to the embodiment shown, the target laser detectors 20 or the supporting cantilevers of the support element 22 overlap with the photodetector 16 arranged therebelow. However, this is irrelevant since the photodetector at the site shown only needs to detect the energy of the work laser beam transmitted through the aperture lying thereabove in any case, said energy being able to pass unimpeded through the aperture 14a and the cantilevers of the support element 22. In this way, it is possible to provide a particularly compact and space-saving stop arrangement 10, which is also attachable in work planes which have little space available.

As a result of the photodetector 16 being spaced apart from the stop 12, the photodetector is arranged in a recessed position relative to the stop 12 which is arranged in the work plane for the purposes of checking the laser beam. This may be advantageous, especially for embodiments where the laser beam is focused into the work plane, since the laser beam then already has a larger diameter in the plane of the photodetector 16 and accordingly strikes the photodetector 16 with a lower intensity. As a result, the load on the photodetector 16 may be reduced and/or use can be made of a photodetector 16 with a lower destruction threshold. Additionally, this recessed arrangement offers the advantage that the incident laser beam has a larger diameter and therefore the laser beam is detected by a larger sensor area, which can increase the accuracy and/or reduce the sensitivity in respect of local variations in the sensor sensitivity of the photodetector.

By contrast, the target laser detectors 20 are arranged closer to the stop 12 and therefore closer to the work plane. However, since the target laser beam typically has a significantly lower power than the work laser beam, damage of the target laser detectors 20 need not be feared even in the case of an arrangement close to the work plane.

Figure 3A:
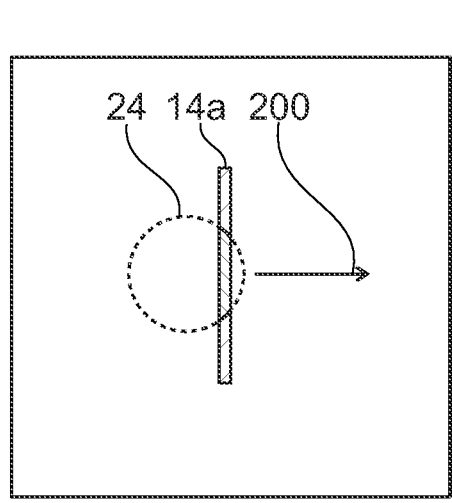
FIG. 3 shows an explanation of an optional embodiment for determining the extent of the laser beam.
Figure 3B:
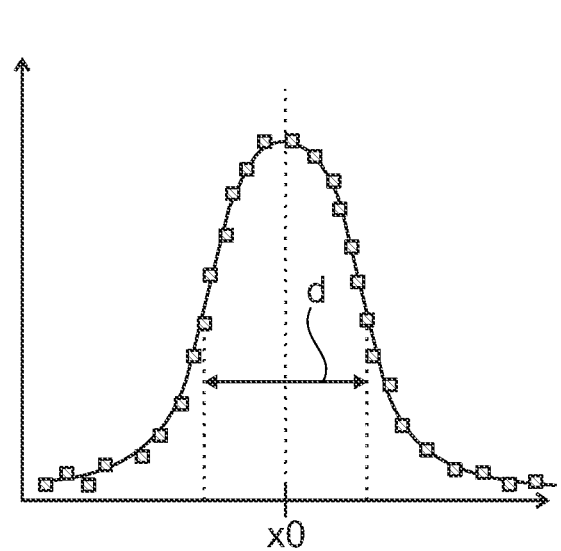

FIGS. 3A and 3B are used below to schematically explain how the extent of the laser beam 24 is determined according to an optional embodiment. FIG. 3A shows a plan view of an aperture 14a and a laser beam 24, the cross-sectional area of which is symbolically represented by a dotted line and which sweeps over the aperture 14a along a scanning direction 200. In this case, the scanning direction 200 runs perpendicular to the longitudinal axis of the slot-shaped aperture 14a. Along the scanning direction 200, the aperture 14a has a dimension, that is to say a width, that is significantly smaller than the mean diameter of the laser beam 24. Accordingly, when sweeping over the aperture 14a along the scanning direction 200, different amounts of the energy or power of the laser beam are transmitted through the aperture 14a at different times and for different relative positions of the laser beam 24 relative to the aperture 14a, while the remaining amount is absorbed or reflected by the stop 12.

In an exemplary diagram, FIG. 3B plots the detector signal of the photodetector 16 arranged below the aperture 14a, said detector signal being proportional to the transmitted energy. The detector signal in arbitrary units on the y axis is plotted against the relative position x of the laser beam 24 vis-à-vis the central axis of the aperture 14a on the x-axis. When the laser beam reaches the aperture 24, the detector signal initially increases in the subsequent measurement points until a maximum has been reached at the position x0, at which the center of the laser beam 24 is located on the central axis of the aperture 14a. The detector signal reduces again if the laser beam is moved further along the scanning direction 200. In order to reliably determine the extent of the laser beam in the scanning direction, the scanning direction must run perpendicular to the longitudinal axis of the aperture 14a. Accordingly, the detector signal follows a curve that is symmetric about the position x0, that is similar to a Gaussian bell curve and that corresponds to a convolution of the laser beam profile with the slot width along the scanning direction, and that facilitates the determination of the beam profile along the dimension of the scanning direction. Deviations of the detector signal from the actual extent of the laser beam 24 or from an ideal Gaussian curve arises for apertures 14a with a finite width. Therefore, accurate knowledge of the extent or width of the aperture 14a is required for the determination of the extent of the laser beam. Subsequently, the extent of the laser beam can be determined as a sum of error functions erf(x). Further, FIG. 3B plots the mean diameter (FWHM) and denotes the latter by d.

Figure 4:
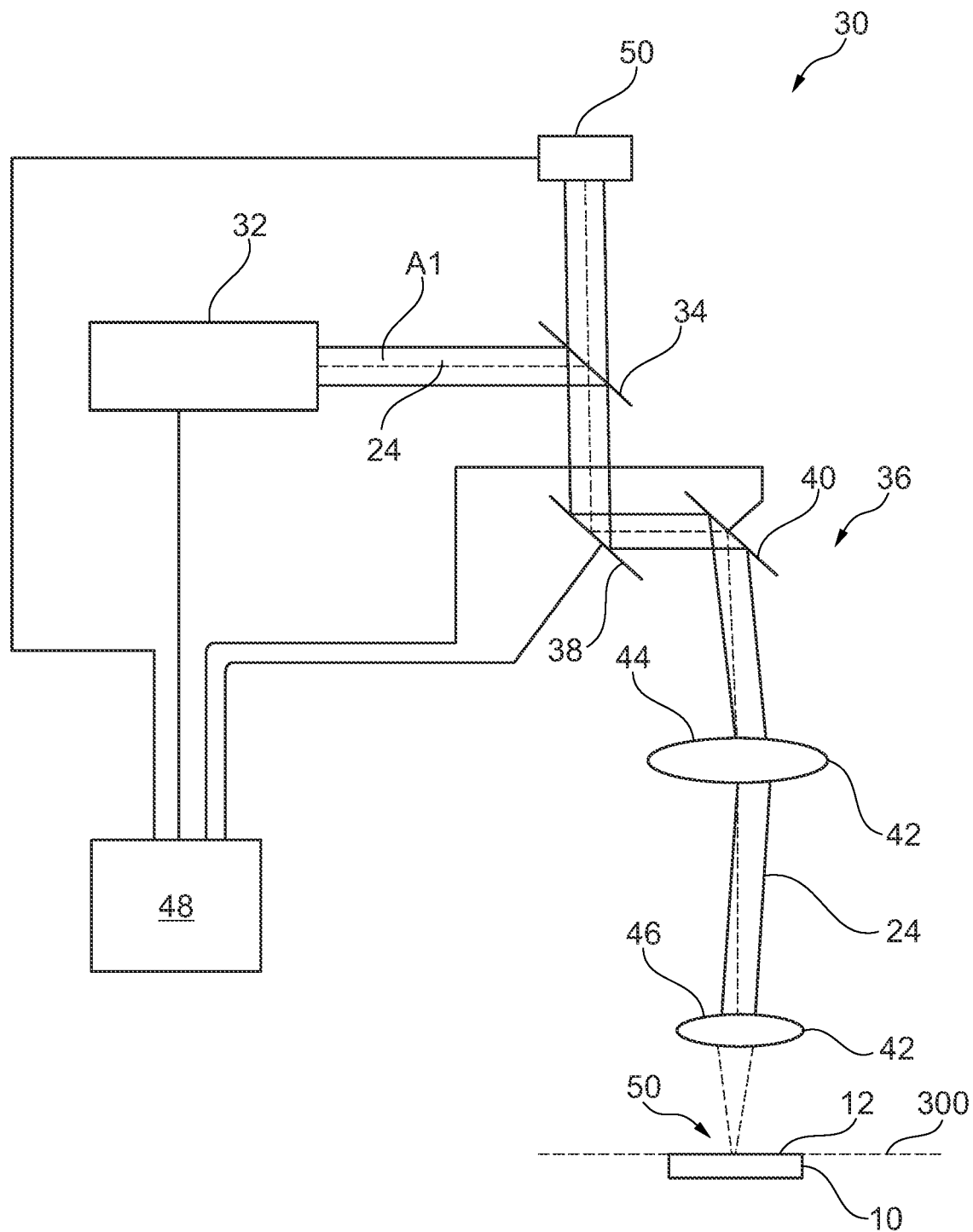
FIG. 4 shows a processing system according to an optional embodiment.

FIG. 4 shows a laser processing system 30 according to an optional embodiment for refractive surgery on an eye. The laser processing system 30 is designed as treatment equipment and serves for example to carry out, using a laser beam or processing laser beam 24, a refractive error correction on an eye of a patient (not shown) by means of a method for refractive surgery. To this end, the laser processing system 30 comprises a laser or a laser source 32, which emits the laser beam 24. The laser beam 24 is designed to act on the cornea of an eye in order to modify the refractive power of the cornea.

The laser beam 24 or the processing beam 24 emitted by the laser 32 along an optical axis A1 is incident on a beam splitter 34 in the process, the latter guiding the laser beam 24 to a deflection unit 36 in the form of a deflection device 36. The deflection unit 36 has two scanning mirrors 38 and 40 which are rotatable about mutually orthogonal axes such that the deflection unit 36 deflects the laser beam 24 in two dimensions. For processing purposes, an adjustable projection optical unit 42 focuses the laser beam 24 onto the processing object or onto or into an eye to be treated. In this case, the projection optical unit 42 has two lens elements 44 and 46.

The eye to be treated is arranged in the work plane 300 for treatment purposes so that the laser beam can be focused thereon. However, an aperture arrangement 10 is arranged in the work plane 300 in FIG. 4 and can be used to check the focused laser beam. To treat the eye, the checking of the laser beam by means of the aperture arrangement 10 can be completed first, the aperture arrangement 10 can then be removed and the treatment of the eye in the work plane can subsequently be started. In this way, the aperture arrangement 10 can be used to examine the laser beam at the position where the eye is also processed or treated by means of the laser beam.

Further, the laser processing system has a control unit 48. The control unit 14 optionally determines the relative position of the focus 50, both perpendicular to the optical axis A1 (by the scanning mirrors 38 and 40) and in the direction of the optical axis A1. Further, the control unit 14 reads a detector 52 which, for example, acts as a co-observation unit and which serves to monitor the processing procedure. Additionally, the laser processing system 30 may have further sensors and/or detectors, in particular an internal energy sensor or energy detector, but these are not shown in the figure. By way of example, the energy sensor may be arranged behind the beam splitter 38 in order to determine the energy of the beam transmitted through the beam splitter. Further, the control unit 48 is connected to the aperture arrangement 10 and designed to read especially the photodetector 16 and optionally the target laser detectors 20 and/or to monitor these. Provided the aperture arrangement 10 is designed and arranged in movable fashion such that, for instance, the laser beam can sweep over the apertures by virtue of the aperture arrangement 10 being displaced in the work plane, it may be advantageous for a corresponding displacement unit also to be connected to the control unit 48 and to be controlled and/or regulated by the latter.

A method for checking a laser beam of a laser processing system is described in exemplary fashion below, without the claimed embodiments however being restricted to this example.

The calibration of the laser system or the checking of the laser beam is implemented in a plurality of steps, but these may also be combined in one scanning pattern in the case of a sufficiently parameterizable laser control:

a) calibrating the deflection device for the generation of the scanning movement;
b) determining the diameter of the laser beam and calculating a target value for the fluence of the laser beam in the work plane for this diameter;
c) measuring the laser energy of the processing laser beam and calculating the fluence from the independent quantities of mean diameters of the laser beam and energy of the laser beam. Comparing target value and actual value;
d) adjusting the energy and repeating b) and c);
e) calibrating a laser beam offset which describes a beam position of the laser beam in the work plane in the case of a neutral position of the scanner mirrors or the deflection device;
f) calibrating a target laser beam offset;
g) calibrating an eye tracker offset.

Figure 5:
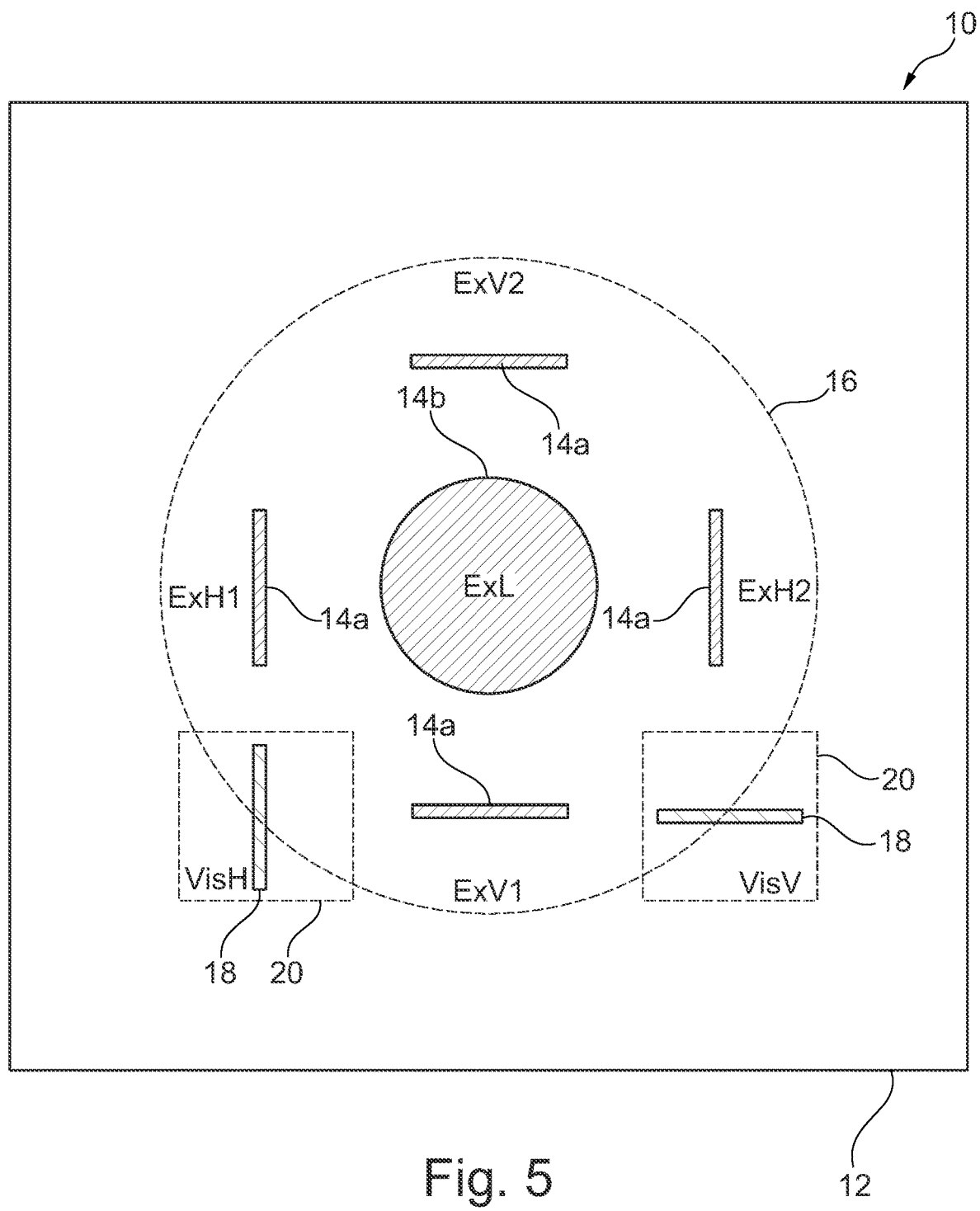
FIG. 5 shows a schematic illustration of the aperture arrangement according to the embodiment from FIG. 2 with further explanations.

The following explanations are provided with reference to FIG. 5, which corresponds to an aperture arrangement according to the embodiment in FIG. 2.

For a better overview, unique labels were assigned to the individual apertures, as is made evident in FIG. 5.

Step 1) The aperture arrangement comprising a stop, a photodetector and two target laser detectors is adjusted in terms of position and alignment in the work plane such that the aperture arrangement is positioned in the work plane, perpendicular to the direction of incidence of the laser beam. The alignment can be implemented using typical adjustment aids of the processing laser. By way of example, these are distance lasers, camera images/video overlays and/or distance sensors.

Step 2) The laser beam is successively driven over the slots or apertures ExH1 and ExH2 with a known increment ds. This yields a respective approximately Gaussian curve for each scan over one of the apertures. The following quantities are derived for both apertures by fitting the known convolution function of intensity curve or detector signal and stop geometry: center x0, mean diameter d (FWHM). Optionally, the amplitude A and the offset y0 of the detector signal are recorded for consistency checks, even though they are not necessarily used further.

Step 3) The comparison of the quantity Distance_H_actual=x0(ExH2)−x0(ExH1) is compared to the known spacing of the slots ExH1 and ExH2 of the stop (distance 100a in FIG. 1), and hence the gain factor gain_H=Distance_Hactual/Distance_H_target of the scanner or deflection device is checked for the horizontal deflection. If there is a deviation between the new and old gain which exceeds a certain tolerance range, the gain factor should be adjusted and steps 1-3 should be repeated.

Step 4) The quantity Offset_Ex_H=x0(ExH2)+x0(ExH1) describes the offset between the position of the centroid of the processing laser beam in the scanner neutral position and a stop center of the stop. The latter is compared to a tolerance range. In the case of deviations, the position of the sensor should be checked using the means from step 1). If the latter is correct, there is a decentration of the scanner or deflection device and the calibration should be terminated.

Step 5) The mean diameters of the laser beam d(ExH1) and d(ExH2) are individually compared to their tolerance range and specified value. A mean value dH is formed for the further calculations. The target fluence $F_{target}$ can be adjusted using the value dH.

Step 6) Steps 2-4 are repeated for the vertical direction on the basis of the apertures ExV1 and ExV2. This supplies the values of dV, Offset_Ex_V and gain_V.

Step 7) In a scanner neutral position or a small region surrounding the latter, the processing laser beam is steered through the central aperture (14b in FIG. 1), which is in the form of a round hole, and the transmitted energy is measured. This supplies the measurement value $E_{Mess}$. The measurement value can be converted using a sensor-inherent calibration factor to the actual value of the energy. This supplies the value $E_{ist}$.

Step 8) The actual fluence $f_{ist}$ is calculated from the values of $E_{ist}$, dH, dV. It is compared with the target fluence $F_{soll}$. In the case of deviations between actual and target fluence, the energy of the processing laser is adjusted and steps 2-7 are repeated with a new setting for the laser energy.

Step 9) Determining the offset of the central aperture ExL (14b in FIG. 1) in the form of a round hole by means of an eyetracker in the vertical and horizontal direction and determining the parameters of Offset_Tracker_V, Offset_Tracker_H. Comparing the offsets with the tolerance ranges defined therefor.

Step 10) Scanning the target laser over the structure VisH and evaluating the position of the centroid $x0_{ist}$(VisH). Since the scanners are calibrated in terms of gain factor from step 3, a difference between actual and target position of the beam centroid arises purely from the offset of the target laser beam: Offset_Vis_H=xO(VisH)−$x0_{target}$(VisH). Comparing Offset_Vis_H with the tolerance range defined therefor.

Step 11) Repeating step 10 for the vertical direction. →Offset_Vis_V.

Figure 6A:
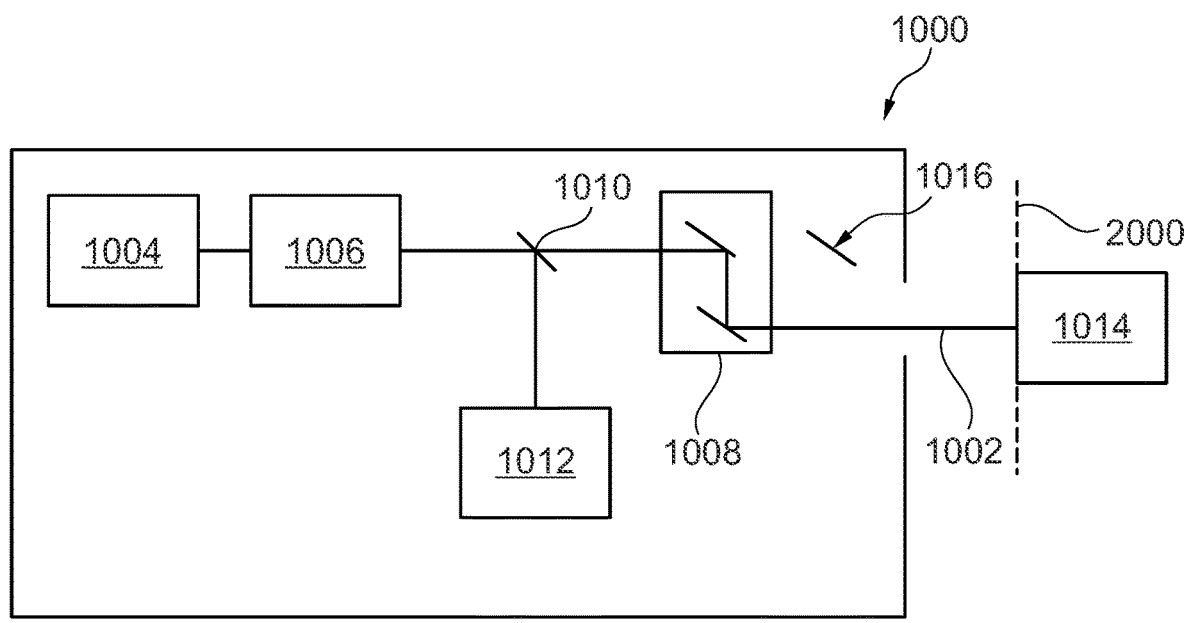
FIGS. 6A and 6B show a laser processing system 1000 according to an optional embodiment in two different modes of operation for characterizing the laser beam 1002.
Figure 6B:
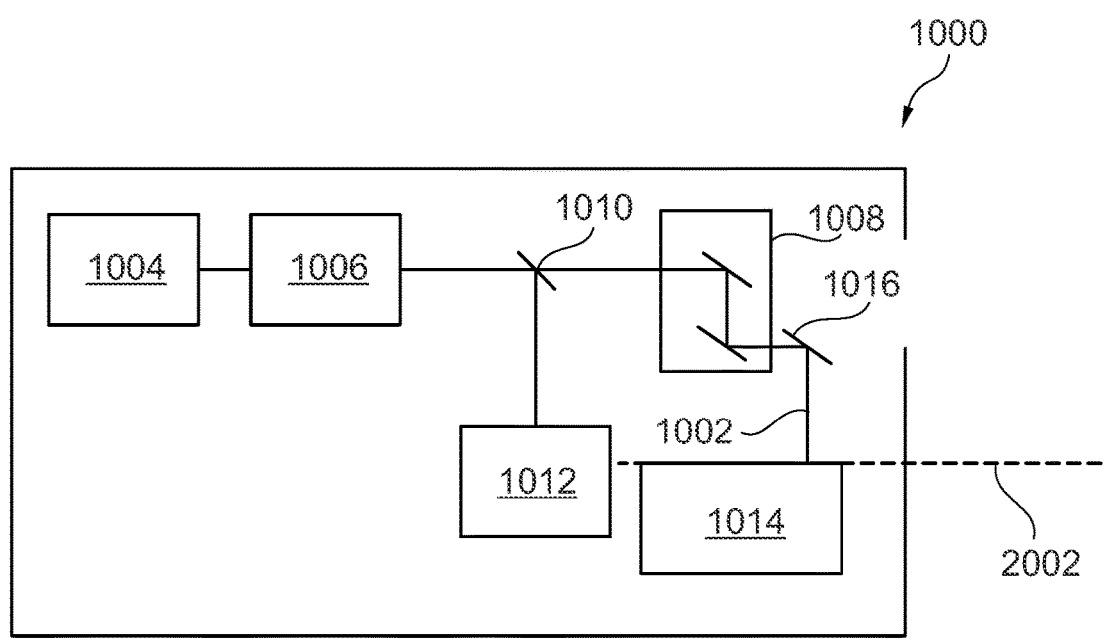

In schematic illustrations, FIGS. 6A and 6B show a laser processing system 1000 according to an optional embodiment in two different modes of operation for characterizing the laser beam 1002.

In this case, the laser processing system 1000 has a laser source 1004 which emits the laser beam 1002, the latter subsequently initially running through a beam shaping device 1006, in which the laser beam 1002 is brought into the desired shape. After the beam shaping device 1006, the laser beam propagates through a deflection device 1008 or scanning device, by means of which the laser beam 1002 is deflectable in such a way that the laser beam 1002 is movable into a work plane 2000 or into a verification plane 2002 in order to carry out the desired processing of a processing object, for instance the treatment of an eye. Optionally, the beam shaping device 1006 is configured to focus the laser beam 1002 into the work plane 2000 or verification plane 2002.

A beam splitter 1010 is arranged in the beam path of the laser beam 1002 between the beam shaping device 1006 and the deflection device 1008, said beam splitter branching off a small part of the laser beam 1002 or laser energy and supplying this to an internal energy sensor 1012. By way of example, the beam splitter 1010 may be designed such that the latter reflects approximately 10% of the energy of the laser beam and transmits the remaining energy, beam splitters with a different ratio also being able to be used for as long as sufficient energy is transmitted for the treatment or processing in the work plane. On the basis of the supplied portion of the laser beam, the energy sensor 12 determines an energy parameter, from which it is possible to derive the energy and/or power of the entire laser beam. Optionally, the laser processing system is configured to use the energy sensor 1012 to carry out a continuous and/or regular determination of the energy parameter during the operation of the laser processing system 1000.

FIG. 6A shows the laser processing system in a first mode of operation for characterizing the laser beam 1002, in which a calibration device 1014 is arranged in the work plane 2000 and determines a calibration parameter for the characterization of the laser beam 1002. In this case, the calibration parameter renders it possible to determine the fluence of the laser beam 1002 in the work plane 2000.

FIG. 6B shows the laser processing system 1000 in a second mode of operation for characterizing the laser beam 1002, in which the calibration device 1014 is arranged in the verification plane 2002. In this case, the verification plane 2002 and also the calibration device 1014 are located within the laser processing system 1000. In the process, a verification parameter is determined in the verification plane 2002 by means of the calibration device 1014, said verification parameter optionally being determined in identical fashion to the calibration parameter, the difference being that the verification parameter is not determined in the work plane 2000 but in the verification plane 2002. In this case, the verification parameter renders it possible to determine the fluence of the laser beam 1002 in the verification plane 2002. In the process, the laser beam 1002 is deflected by a deflection element 1016 such that said laser beam is incident not on the work plane 2000 but on the verification plane 2002. By way of example, to this end, the deflection element 1016 may be in the form of a mirror and can be moved into the beam path of the laser beam 1002 by the laser processing system 1000. By way of example, the deflection element may be arranged in displaceable or pivotable fashion in order to be able to be moved into and out of the beam path. Once the determination of the verification parameter has been completed, the deflection element 1016 may be moved out of the beam path again such that the laser beam 1002 can propagate into the work plane again.

Optionally, the verification parameter is determined directly after the determination of the calibration parameter in order to minimize the risk of intervening changes.

Then, the laser processing system 1000 can determine a deviation factor on the basis of the calibration parameter and the verification parameter, it being possible to relate the two parameters or measurement values based thereon, for instance the determined fluence values, to one another using said deviation factor.

Subsequently, the laser processing system 1000 may perform a verification of the laser beam 1002 by virtue of only determining the verification parameter, comparing the latter to a target value and carrying out a check on the basis of the energy parameter as to whether the energy of the laser beam 1002 also corresponds to the target value. As a result, the laser beam 1002 can even be checked if the work plane is not accessible for a determination of the calibration parameter.

In a processing mode, in which a processing object is processed by means of the laser beam, the deflection element 1016 is likewise arranged outside of the beam path, for example as shown in FIG. 6A, but in the processing mode it is not the calibration device 1014 that is arranged in the work plane 2000, but a processing object (not shown).

Figure 7A:
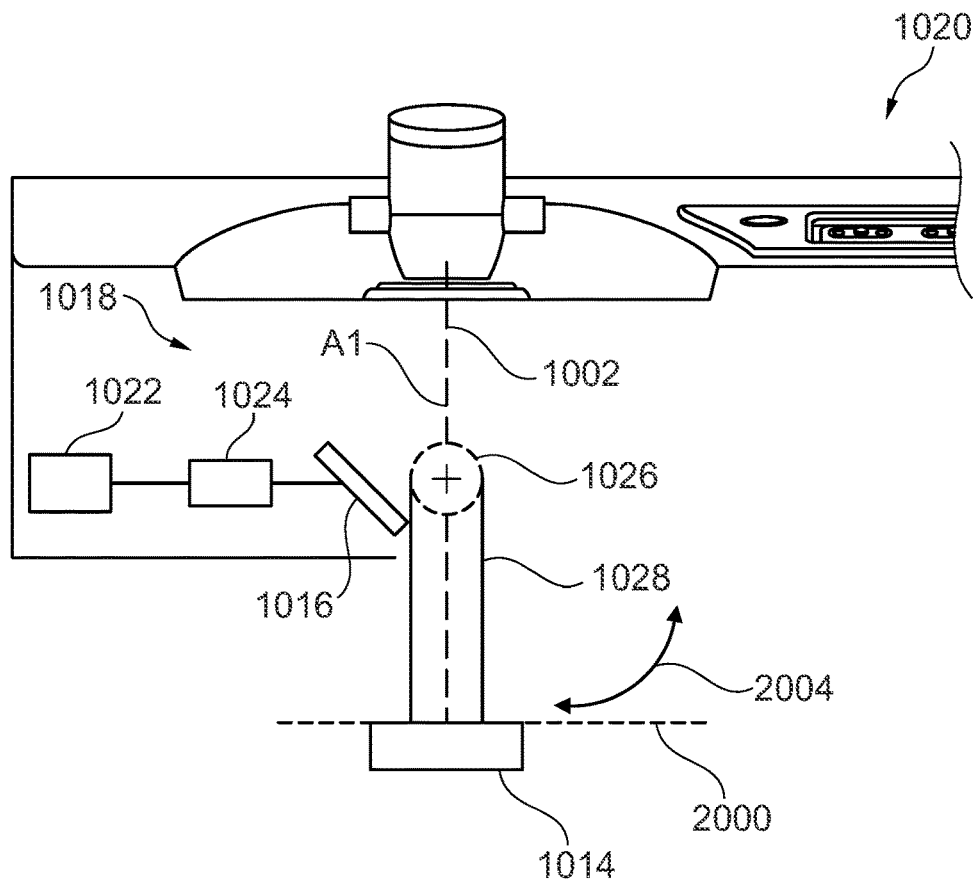
FIGS. 7A and 7B show schematic illustrations of a processing head 1020 of a laser processing system 1000 according to an optional embodiment.
Figure 7B:
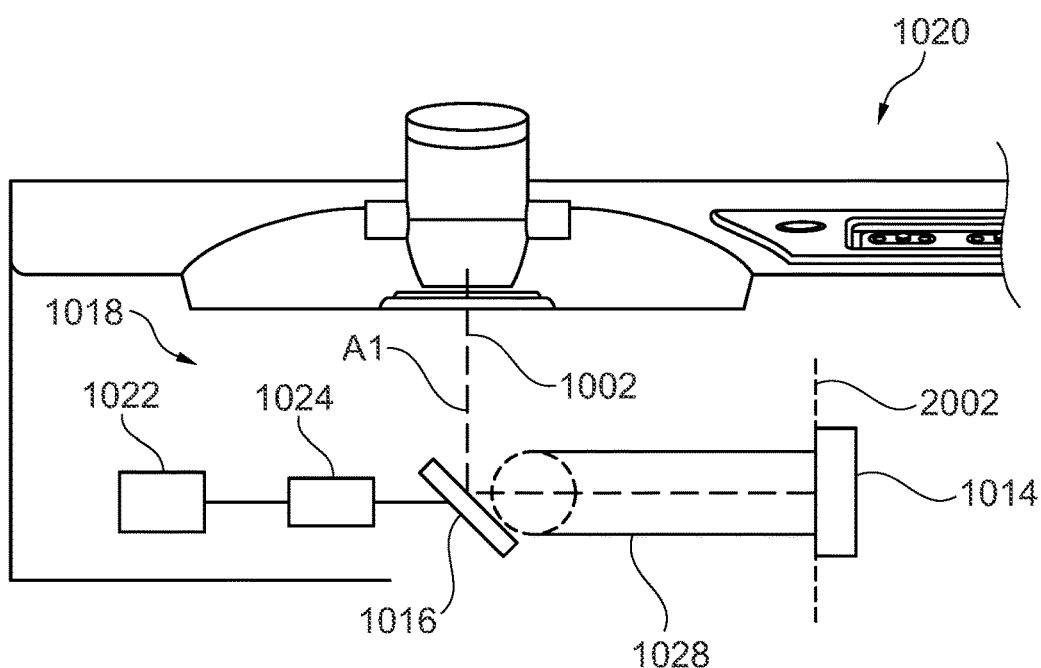

In schematic illustrations, FIGS. 7A and 7B show a processing head 1020 of a laser processing system 1000 according to an optional embodiment in two modes of operation for the characterization of the laser beam 1002.

In this case, the processing head 1020 is designed to emit the laser beam 1002 such that the latter propagates along the optical axis A1 and is incident either in the work plane 2000 or in the verification plane 2002.

Further, on the processing head 1020, the laser processing system 1000 has an arrangement for being able to choose an arrangement of the calibration device 1014 in the work plane 2000 and in the verification plane 2002 and for being able to choose a positioning of the deflection element 1016 within or outside of the beam path or optical axis A1 of the laser beam 1002. To this end, the arrangement has a drive 1022 and a guide 1024 in order to bring the deflection element 1016 from a position outside of the beam path (FIG. 7A) into a position in the beam path (FIG. 7B), and vice versa.

Further, the laser processing system 1000 has a pivoting device for pivoting the calibration device 1014 from the work plane 2000 into the verification plane 2002, and vice versa. By way of example, to this end the calibration device 1014 may be fastened to a pivot joint 1026 by way of an arm 1024, the arm 2024 being able to be pivoted about said pivot joint, as indicated by the curved arrow 2004. Naturally, the arrangement is formed and/or arranged in such a way that the laser beam is not impeded or blocked by the arrangement or any one of its components in all of the modes of operation.

In a mode of operation for processing a processing object or for treating an eye, the calibration device 1014 for example may be pivoted into the verification plane and the deflection element 1015 may be arranged outside of the beam path.

A calibration of the laser beam 1002 of a laser processing system 1000 is described below on the basis of an example, without the claimed embodiments being restricted to the following example.

In particular, the following explanation relates to linking the calibration with the calibration device in the work plane (external position) with the verification by means of the calibration device in the verification plane (internal position).

1) Initially, the calibration or characterization of the laser beam is carried out by means of the calibration device in the work plane (determining a calibration parameter) without an additional optical element or deflection element. Moreover, an energy parameter is determined in this case as a reference value for the internal energy sensor (Eint,0) according to a calibration method, and the laser energy is adjusted until the actual fluence $F_{actual\_external}$ is within the tolerances of the target fluence ($F_{target,\ external}$).

2) Immediately subsequently, the test is carried out on the same calibration device, but in a verification plane within the laser processing apparatus, optionally at a constant work distance in relation to the aperture of the laser source, and a verification parameter is determined. By way of example, this may be realized by a rigid pivoting mechanism or by mechanical or magnetic stops. In this case, an additional optical element is used as a deflection element, in order to fully steer the laser beam onto the internal position of the calibration device in the verification plane. The additionally introduced deflection element is arranged downstream of the last optical element of the beam path (in the beam direction).

This determination of the verification parameter by means of an internal fluence measurement (this measurement is explicitly not a calibration) is carried out at a fixed energy setting in respect of the energy found in step 1), that is to say at $E_{int,0}$, and supplies a fluence value $F_{actual,internal}$.

This value differs from the fixed value $F_{target,external}$ on account of the properties of the additional deflection element, for instance the reflectivity of the deflection element in the form of a mirror. This is used to determine a deviation factor, by means of which these effects can be calculated:

$$R = F_{actual,internal}/F_{target,external}.$$

3) The characterization of the laser beam or the calibration of the laser system can subsequently be carried out exclusively by way of the internal position (that is to say, without the necessity of arranging the calibration device in the external position), that is to say by way of the verification parameter, with the target value of the fluence being calculated by way of the deviation factor R determined in 2):

$$F_{target,internal} = R \cdot F_{target,external}.$$

4a) The calibration interval for determining the deviation factor R (steps 1 & 2) can be defined in such a way that a degradation of the additional deflection element does not influence the calibration accuracy (e.g., by defining adequate time intervals/number of tests).

4b) Ideally, a possible degradation of the deflection element, for instance a waning reflectivity, can be checked by continuously monitoring the verification parameter relative to that of the energy sensor in the laser arm, that is to say of the energy parameter: Optionally, this is implemented by continuous comparison of the measurement signals $F_{actual,internal}$ and $E_{int,current}$ (cross-calibration of the calibration device with the current measurement value of the internal energy sensor in the case of a calibration device with continuous measurement value).

4c) Independently thereof, a possible degradation of the deflection element may be monitored in a different spectral range to that of the processing laser. To this end, a transmission or reflectivity measurement of the deflection element can be carried out regularly. Since a degradation of an optical element at this position, that is to say as a last optical element in front of the work plane, may typically arise by surface damage on the coated side (by the treatment laser) or by contamination, for example by droplets of the rinsing fluid used in refractive surgery, a degradation may also be determined in a different spectral range. By way of example, a degradation may be implemented by means of an illumination device and a camera and/or by using the scanned target lasers typically present in such systems.

However, degradation only can be determined in this way; a quantification can be attained by means of the method presented in 4b) or in step 1)-2). However, the determination alone may serve to deactivate the laser processing system and/or terminate a treatment and/or output an appropriate notification that a check is required.

Figure 8A:
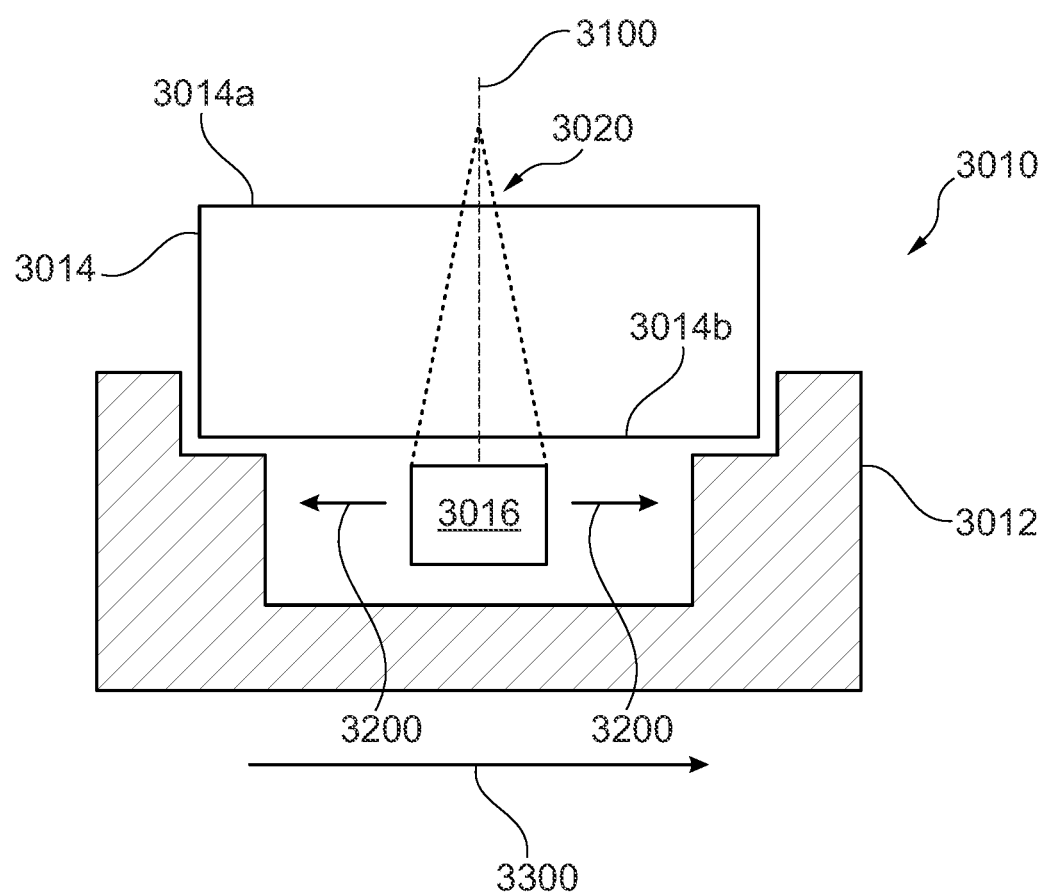
FIGS. 8A and 8B show an apparatus for characterizing a laser beam according to an optional embodiment.

FIG. 8A shows an apparatus 3010 for characterizing a laser beam (see FIG. 8B) in a schematic illustration. The apparatus 3010 has a test object holder 3012, which holds a test object 14 in a specified position. The test object holder 3012 is configured in such a way here that a laser beam can be incident on a surface on the top side 3014a of the test object 3014 from the side distant from one of the test object holders 3012.

A sensor 3016 of a measuring device 3018 (not shown) is arranged below the test object 3014, that is to say on the side facing the test object holder 3012. In addition to the sensor 3016, the measuring device 3018 may comprise even further elements, for instance a control and/or evaluation unit.

The sensor 3016 is designed as a confocal-chromatic sensor which is designed and arranged such that the latter radiates electromagnetic radiation in the visible and/or infrared spectral range along the optical axis 3100 of the sensor 3016 into the test object 3014 via the lower side 3014b, said electromagnetic radiation being referred to as measurement light below. As is conventional for confocal-chromatic sensors, the radiated-in measurement light is focused in such a way that different wavelengths or different spectral components are focused at different focal lengths and accordingly differ in terms of their penetration depth into the test object 3014.

Typically, the shorter wavelength spectral components are focused with a shorter focal length while the longer wavelength components are focused with a longer focal length, even though other embodiments may likewise also be suitable. The light cone of the focused measurement light is represented in exemplary fashion by the dotted line.

By means of the sensor 3016, it is possible to measure the thickness of the test object 3014 by virtue of detecting, evaluating and comparing the components of the measurement light reflected and/or scattered at the lower side 3014b and at the top side 3014a. On account of the different penetration depths of the various spectral components, the two reflections or scatterings at the top side 3014a and lower side 3014b are different from one another such that the distance of the reflection plane or scattering plane from the sensor 3016 can be determined from the different spectral composition of the two reflections or scatterings, and the thickness of the test object 3014 can be determined therefrom.

It is self-evident that the test object 3014 needs to be at least partly, ideally virtually completely transparent to the measurement light. By way of example, the test object 3014 is formed from PMMA since PMMA has a suitable transparency to the measurement light and moreover is processable by means of UV laser radiation.

The site of the test object 3014 which is measured by the sensor 3016 or at which the thickness of the test object 3014 is determined is referred to as test site 3020. To also determine the thickness of the test object 3014 at other positions of the test object 3014 or at other test sites 3020, the test object 3014 can be at least partly scanned by means of a relative movement between the test object 3014 and the sensor 3016. In this case, the thickness of the test object 3014 is the spatial extent of the test object 3014 parallel to the optical axis 3100. The thickness may vary at different sites of the test object 3014. To measure the thickness at a plurality of test sites 3020, the sensor 3016 and/or the test object holder 3012 may be moved in one or preferably two dimensions perpendicular to the optical axis 3100, as indicated by arrows 3200 and 3300.

Figure 8B:
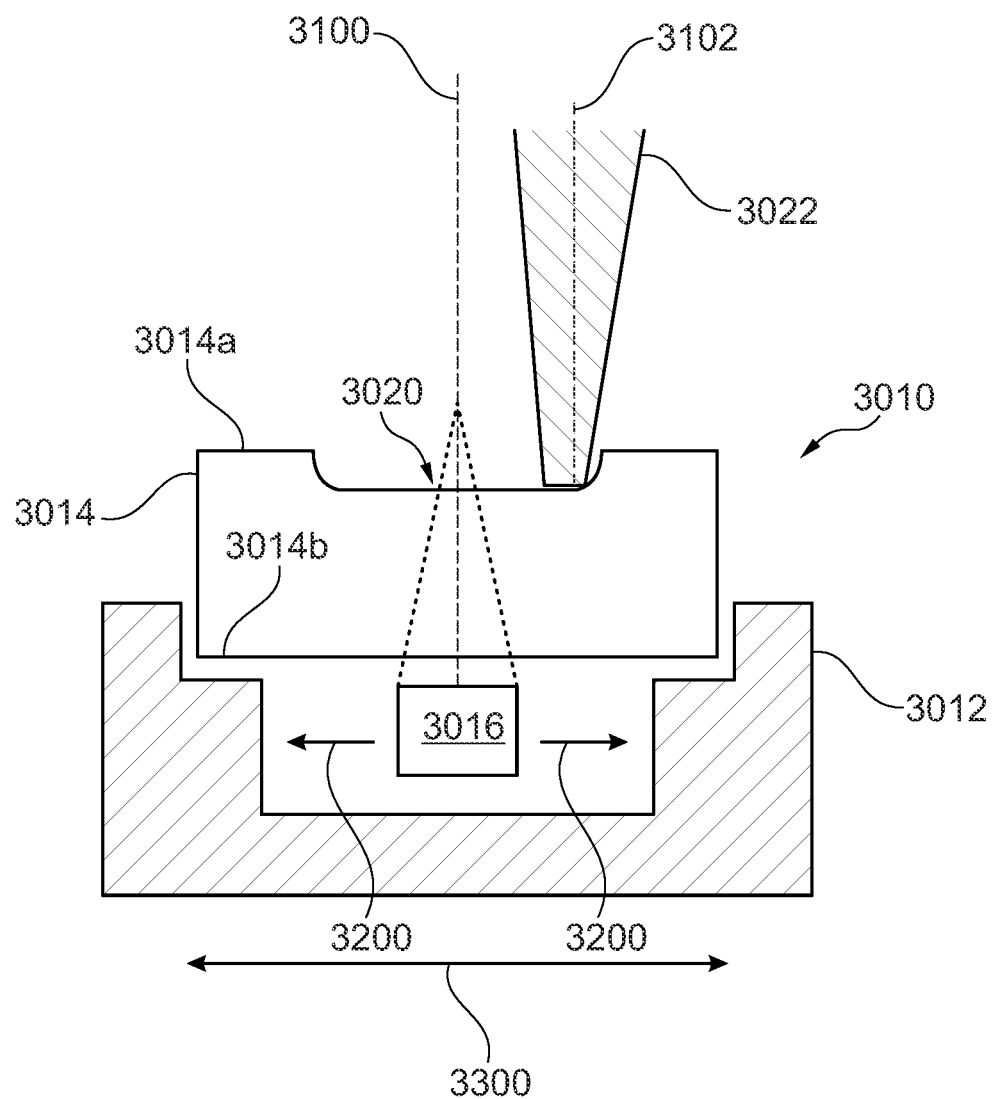

FIG. 8B shows the apparatus of the embodiment according to FIG. 8A, a laser beam 3022 additionally being shown, the latter being used or having been used to ablate material from the top side 3014a of the test object 3014. Optionally, the laser beam 3022 has a central wavelength in the ultraviolet spectral range, for example at 193 nm. Optionally, the laser beam 3022 is provided by an ArF excimer laser, even though other laser sources may also be suitable for providing a suitable laser beam 3022.

According to the shown embodiment, the laser beam 3022 is incident on the test object 3014 along the optical axis 3102, the optical axis 3102 of the laser beam 3022 being parallel to the optical axis 3100 of the sensor 3016. According to other embodiments, the laser beam may also be incident under a different angle.

The test object 3014 at least partly consists of a material that is suitable to at least partly absorb the laser radiation. This facilitates material ablation of the test object 3014 by means of the laser beam 3022. As already explained above, the test object is optionally formed from PMMA since the latter has a high optical density in the ultraviolet spectral range and further is sufficiently transparent to the measurement light. The thickness of the test object 14 is optionally chosen in such a way here that, even after material ablation for the characterization of the laser beam 3022, the thickness of the test object 14 is sufficient to avoid the laser radiation passing through to the sensor 3016. As a result, damage to the sensor as a result of the laser beam 3022 can be avoided.

If the position of the sensor 3016 and its axis 3100 relative to the focus position of the laser beam 3022 and its axis 3102 are known or specified, for example by way of a suitable stop on the laser by way of the test object holder 3012, the acceptable position of the test site 3020 relative to the laser beam 3022 can be ensured before the thickness measurement, for example to the effect of the test object 3014 having been inserted correctly into the specimen holder 3012.

On account of the material ablation by the laser beam 3022, the thickness of the test object 3014 has changed at the processed sites. The change of the thickness can be determined by means of the sensor 3016, for example by virtue of the thickness being determined before and after and/or before and during the processing with the laser beam 3022. On account of the high sensitivity of the confocal-chromatic sensor 16, a change in the thickness above 100 nm or even less can optionally already be determined.

The material ablation by the laser beam 3022 is optionally implemented with a predetermined shot number or laser pulse number for each test site 3020. Therefore, the material ablation per pulse or shot can be determined from the change in the thickness of the test object 3014 since the number of shots or pulses that impinged on the test site 3020 is known. Additionally, other test sites 3020 can each have a different number of pulses or shots impinging thereon in order to obtain further measurement data by comparing the material ablation or the change in thickness at the different test sites, and in order to be able to determine the change in the thickness even more reliably.

Figure 9:
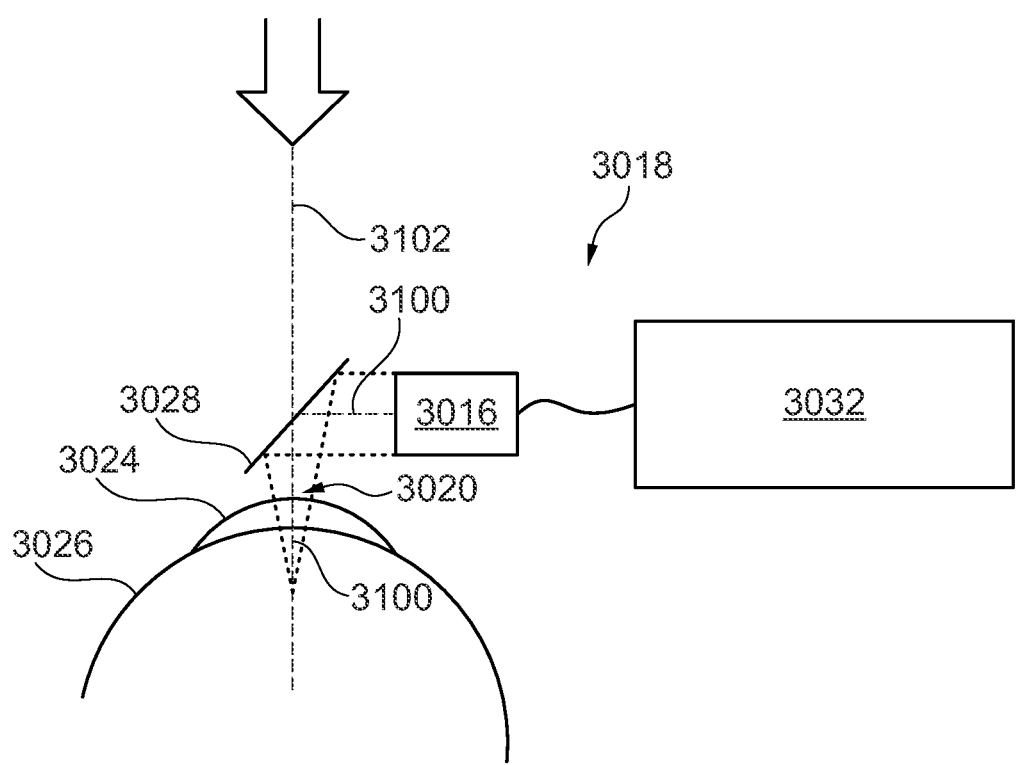
FIG. 9 shows an apparatus according to an optional embodiment for characterizing the laser beam during refractive correction on a cornea.

FIG. 9 shows a further embodiment, in which the laser beam (not shown) is characterized during the application to the cornea 3024 of a human eye 3026. Expressed differently, the cornea 3024 adopts the function of the test object 3014 according to this optional embodiment and should therefore likewise be considered a test object 3014 within the meaning of this patent application.

According to this optional embodiment, the cornea 3024 is subjected to refractive correction by means of the laser beam (not shown), for the purposes of which the laser beam is incident on the cornea 3024 along the optical axis 3102 as indicated by the arrow 3104.

In the beam path of the laser beam, that is to say in the optical axis 3102, a beam splitter 3028 is arranged in front of the cornea 3024, said beam splitter being tilted by 45° with respect to the optical axis 3102 according to this embodiment, with other angles also being possible according to other embodiments. Optionally, the beam splitter 3028 is virtually completely transparent at the central wavelength of the laser beam such that the laser beam can pass through the beam splitter virtually unimpeded, without having to accept noteworthy power losses.

By contrast, the beam splitter 3028 is optionally highly reflective to the wavelengths of the measurement light emitted by the confocal-chromatic sensor 3016. Alternatively or in addition, the beam splitter 3028 may also be designed as polarization splitter which merges differently polarized processing laser and measurement light. According to an optional embodiment, the beam splitter 3028 is in the form of a measurement light reflector which is able to be intermittently pivoted in in order to realize measurements or characterizations of the laser beam 3022 between individual pulses or pulse sequences of the laser beam 3022.

According to this embodiment, the optical axis 3100 of the sensor 3016 is arranged here at right angles to the optical axis 3102 of the laser beam. In this case, the measurement light is directed at the beam splitter 3028 which deflects the measurement light to the test site 20 on the cornea 3024 which is processed by the laser beam.

The light reflected and/or scattered at the test site 3020 or cornea 3024 is likewise reflected by the beam splitter and cast back to the sensor 3016. Thereupon, the sensor 3016 can detect the cast-back measurement light. The measuring device 3018 which also has a control and evaluation unit 3032 in addition to the sensor determines the change in the thickness of the cornea 3024 at the test site 3020 on the basis of the data determined by the sensor and can characterize the laser beam on the basis thereof. A check of the position of the corneal surface in relation to the sensor 3016 and/or focus of the laser beam 3022, which is also possible, is advantageous for realizing correct processing and thickness measurements. Should in the case of a fault the cornea move out of a predefined work range on the axis 3100, the laser processing and thickness measurement can be readjusted and/or terminated and/or at least be interrupted.

Not shown is an alternative optional embodiment in which the sensor 3016 is positioned laterally to the incident laser beam 3022 in order to be able to measure test sites 3020 processed by the laser beam 3022 without needing the light of the sensor 3016 and the laser beam 3022 to be overlaid by means of optical components, for example by virtue of the axes 3100 and 3102 forming an angle so as to intersect at a test site 3020, or even without an overlap by virtue of the sensor 3016 being successively laterally displaced in order to measure a test site 3020 previously processed by the laser beam 3022.

According to an optional embodiment, the measuring device is also connected to a control device (not shown) of the laser source and can if necessary intervene in the closed-loop and/or open-loop control of the laser source using the data from the characterization of the laser beam, for example in order to increase and/or reduce the power of the laser beam.

Using the shown embodiment it is therefore possible to carry out a real-time characterization of the laser beam, which may be used for closed-loop control of the laser beam for example.

Figure 10A:
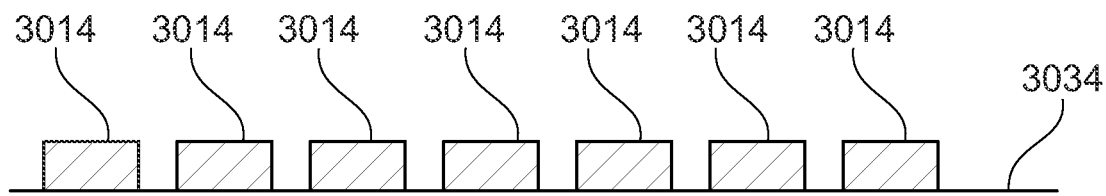
FIGS. 10A to 10C show various optional embodiments of test objects.
Figure 10B:
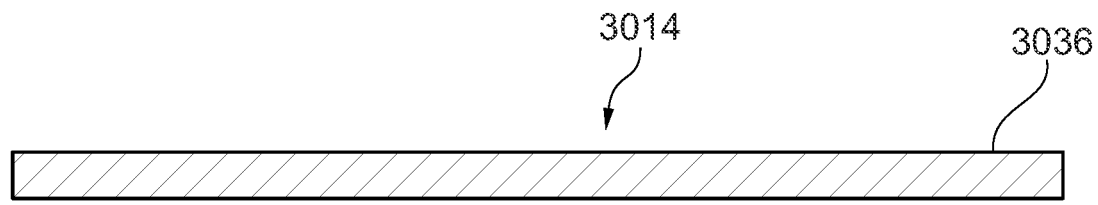
Figure 10C:
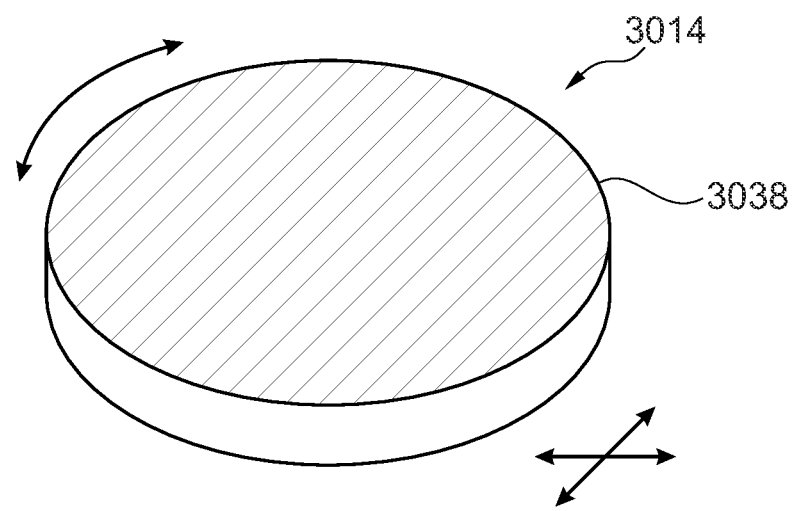

FIGS. 10A to 10C show various optional embodiments for the provision of test objects 3014 in schematic illustrations.

According to the embodiment in FIG. 10A, a plurality of block-like test objects 3014 are arranged on a substrate 34. By way of example, the substrate 3034 can be in the form of a flexible film. By way of example, such an embodiment facilitates an automated supply of test objects 3014 to the test object holder by virtue of the substrate 3034 being moved by way of rollers, for example.

According to the embodiment shown in FIG. 10B, the test object 3014 itself is in the form of a film 36. Different parts of the film can be used as test sites 3020 by way of suitable repositioning of the film 36. In this case, the film 3036 should be chosen to be sufficiently thick to prevent the laser beam 3022 from passing through the film 3036 and prevent the laser beam from being incident on a sensor 3016 possibly arranged below the film.

According to the embodiment shown in FIG. 10C, the test object 3014 is in the form of a disk 3036, the disk being substantially larger than an individual test site 3020. By displacing and/or rotating the disk 36 it is subsequently possible to select different sites on the disk 3036 for impingement by the laser beam such that a multiplicity of test sites 3020 are able to be housed on the test object 3014 or on the disk 3028, optionally more than 1000 test sites 3020.

LIST OF REFERENCE SIGNS

10 Stop arrangement
12 Stop
14, 14a, 14b Aperture for the work laser beam
16 Photodetector
18 Aperture for the target laser beam
20 Target laser detector
22 Carrier element
24 Laser beam
30 Laser processing system
32 Laser source
34 Beam splitter
36 Deflection device
38 Scanning mirror
40 Scanning mirror
42 Projection optical unit
44 Lens
46 Lens
48 Control unit
50 Focus
52 Detector for monitoring the processing procedure
100a, 100b Predetermined distance between two apertures 14a
200 Scanning direction
300 Work plane
1000 Laser processing system
1002 Laser beam
1004 Laser source
1006 Beam shaping device
1008 Deflection device
1010 Beam splitter
1012 Energy sensor
1014 Calibration device
1016 Deflection element
1018 Arrangement for moving the deflection element
1020 Processing head
1022 Drive
1024 Guide
1026 Pivot joint
1028 Arm
2000 Work plane
2002 Verification plane
2004 Pivoting movement
3010 Apparatus for characterizing a laser beam
3012 Test object holder
3014 Test object
3014a Top side of the test object
3014b Lower side of the test object
3016 Sensor
3018 Measuring device
3020 Test site
3022 Laser beam
3024 Cornea
3026 Eye
3028 Beam splitter
3032 Control and evaluation unit
3034 Substrate
3036 Film
3038 Disk
3100 Optical axis of the sensor
3102 Optical axis of the laser beam
3200 Movement direction of the sensor
3300 Movement direction of the test object holder
A-A' Indicators of the cross-sectional profile
B-B' Indicators of the cross-sectional profile
A1 Optical axis of the laser beam

The invention claimed is:

1. A method for characterizing at least one laser beam of a laser processing system, the method comprising:
    a) providing an aperture arrangement with a plurality of apertures in a work plane of the laser processing system, in such a way that the apertures extend within the work plane;
    b) scanning the laser beam over the aperture arrangement along a scanning direction parallel to the work plane in such a way that the laser beam sweeps at least partly over the at least two of the apertures successively in time;
    c) determining a respective energy of the laser beam transmitted through the apertures during a scanning procedure; and
    d) determining an extent of the laser beam along the scanning direction on the basis of the respectively determined energy of the laser beam transmitted through a first aperture of the plurality of apertures and determining an energy parameter of the laser beam on the basis of the determined energy of the laser beam transmitted through a second aperture of the plurality of apertures;
    the first aperture having a predetermined extent along the scanning direction which is smaller than a mean diameter of the laser beam in the work plane and the second aperture having an extent which is greater than the laser beam in the work plane and which is configured to substantially fully transmit the laser beam.

2. The method as claimed in claim 1, wherein the aperture arrangement further comprises a third aperture of the plurality of apertures which has a predetermined extent along the scanning direction which is smaller than the mean diameter of the laser beam in the work plane and which is arranged at a predetermined distance from the first aperture along the scanning direction, and wherein the method further comprises:
    determining an alignment parameter of the laser processing system using the predetermined distance of the third aperture from the first aperture.

3. The method as claimed in claim 2, wherein determining the extent of the laser beam along the scanning direction is further implemented on the basis of the determined energy of the laser beam which has been transmitted through the third aperture and optionally comprises the calculation of a mean of the extents of the laser beam determined on the basis of the first and the third aperture.

4. The method as claimed in claim 1, wherein the scanning of the laser beam is implemented in a first scan portion and in a second scan portion, the scanning direction in the first scan portion running along a first dimension parallel to the work plane and the scanning direction in the second scan portion running along a second dimension parallel to the work plane.

5. The method as claimed in claim 4, wherein the first aperture has the predetermined extent along the scanning direction in the first scan portion and wherein the aperture arrangement has an additional aperture of the plurality of apertures which has a predetermined extent along the scanning direction in the second scan portion which is smaller than the mean diameter of the laser beam in the work plane.

6. The method as claimed in claim 5, wherein the plurality of apertures comprise at least two apertures for each scan portion, the at least two apertures having a predetermined extent along the respective scanning direction which is smaller than the mean diameter of the laser beam in the work plane and being arranged at a predetermined distance from one another along the respective scanning direction.

7. The method as claimed in claim 1, wherein the method is used to characterize the laser beam and further used to characterize a target laser beam of the laser processing system.

8. The method as claimed in claim 1, further comprising a determination of a fluence and/or an intensity of the laser beam in the work plane using the determined extent of the laser beam and the determined energy parameter of the laser beam.

9. The method as claimed in claim 1, further comprising an adjustment of a laser parameter and a repeated implementation of steps b) to d) after the adjustment of the laser parameter.

* * * * *